(12) United States Patent
Katayama et al.

(10) Patent No.: US 9,174,906 B2
(45) Date of Patent: Nov. 3, 2015

(54) PROCESS FOR PRODUCING OPTICALLY ACTIVE SECONDARY ALCOHOL

(71) Applicants: KANTO KAGAKU KABUSHIKI KAISHA, Chuo-ku, Tokyo (JP); NATIONAL UNIVERSITY CORPORATION HOKKAIDO UNIVERSITY, Sapporo-shi, Hokkaido (JP)

(72) Inventors: Takeaki Katayama, Soka (JP); Kunihiko Tsutsumi, Soka (JP); Kunihiko Murata, Soka (JP); Takeshi Ohkuma, Sapporo (JP); Noriyoshi Arai, Sapporo (JP)

(73) Assignees: KANTO KAGAKU KABUSHIKI KAISHA, Tokyo (JP); NATIONAL UNIVERSITY CORPORATION HOKKAIDO UNIVERSITY, Sapporo-Shi (JP)

( * ) Notice: Subject to any disclaimer, the term of this patent is extended or adjusted under 35 U.S.C. 154(b) by 0 days.

(21) Appl. No.: 14/340,790

(22) Filed: Jul. 25, 2014

(65) Prior Publication Data
US 2015/0031920 A1 Jan. 29, 2015

(30) Foreign Application Priority Data

Jul. 26, 2013 (JP) ................. 2013-156036

(51) Int. Cl.
C07C 41/26 (2006.01)
C07C 29/145 (2006.01)
B01J 31/18 (2006.01)
C07B 53/00 (2006.01)

(52) U.S. Cl.
CPC ............ *C07C 41/26* (2013.01); *B01J 31/1815* (2013.01); *C07B 53/00* (2013.01); *C07C 29/145* (2013.01); *C07B 2200/07* (2013.01); *C07C 2531/28* (2013.01)

(58) Field of Classification Search
None
See application file for complete search history.

(56) References Cited

U.S. PATENT DOCUMENTS 8,212,037 B2 * 7/2012 Noyori et al. ............... 546/2

FOREIGN PATENT DOCUMENTS

| EP | 1323724 A2 | 7/2003 |
|---|---|---|
| JP | H08225466 A | 5/1995 |
| JP | H11189600 | 7/1999 |
| JP | 2007536338 A | 2/2005 |
| JP | 2011051929 | 3/2011 |
| WO | WO2006046508 A1 | 5/2006 |
| WO | WO2006103756 A1 | 10/2006 |

OTHER PUBLICATIONS

Ohkuma, T. Asymmetric hydrogenation of ketones: Tactics to achieve high reactivity, enantioselectivity, and wide scope. Proc. Jpn. Acad., Ser B 86: 202 (2010).
Extended European Search Report for EP1323724A2, Jul. 2, 2003, Kanto Kagaku Kabushiki Kaisha.

* cited by examiner

*Primary Examiner* — Brian J Davis
(74) *Attorney, Agent, or Firm* — Brian S. Boyer; Syndicated Law, PC

(57) ABSTRACT

Methods are provided for producing an optically active secondary alcohol at a high optical purity by hydrogenating a substrate carbonyl compound at a high efficiency using as a catalyst a ruthenium complex bearing as a ligand certain optically active diphosphine compound and a readily synthesized amine compound. For example, aromatic ketones and heteroaromatic ketones are reacted with hydrogen and/or a hydrogen donating compound in the presence of the ruthenium complex.

17 Claims, No Drawings

PROCESS FOR PRODUCING OPTICALLY ACTIVE SECONDARY ALCOHOL

FIELD OF INVENTION

The present invention relates to a method of producing optically active secondary alcohols, in particular optically active bioactive compounds that are used for medicaments, agrochemicals, and the like, or optically active secondary alcohols that are useful as intermediates for synthesizing a liquid crystal.

BACKGROUND ARTS

An optically active alcohol is useful as a chiral building block for synthesizing various optically active compounds. In general, an optically active alcohol is produced by optical resolution of a racemate, or an asymmetrical synthesis using a biological catalyst, asymmetric organocatalyst or asymmetric organometallic catalyst. The synthesis of an optically active alcohol by these asymmetric syntheses is considered to be an essential technique for production of optically active alcohol in a large scale.

Among the means for obtaining a optically active alcohol at a high efficiency, a method of asymmetric hydrogenation of a carbonyl compound in the presence of a ruthenium metal complex bearing a optically active diphosphine compound such as 2,2'-bis(diphenylphosphino)-1,1'-binaphthyl (BINAP), a optically active diamine compound in a ethylenediamine form, and a base such as a hydroxide of an alkaline metal or alkaline earth metal (Patent Literature 1), as well as a method of asymmetric hydrogenation of a carbonyl compound in the presence of an optically active diphosphine compound such as BINAP, a ruthenium metal complex bearing an ethylenediamine-type optically active diamine compound as a ligand, and a base such as a hydroxide of an alkaline metal or alkaline earth metal are disclosed (Patent Literature 2). However, in order to improve optical purity of the product of these method, i.e., the optically active alcohol, both diphosphine and diamine ligands have to be made optically active. Most of such optically active compounds used as ligands are expensive for their long synthetic pathways. Consequently, the complex is also expensive, producing a problem in its industrial use.

On the other hand, ruthenium complexes that have an achiral amine and an optically active diphosphine as ligands has also been known.

A ruthenium complex that has an optically active diphosphine and 2-picolylamine (PICA) as ligands can be synthesized at low cost because PICA is not an optically active compound. This complex is known to act as a catalyst for asymmetric transfar hydrogenation using 2-propanol as hydrogen source, reducing a ketone at a high efficiency (Patent Literature 3). In this literature, acetophenone is reacted under pressurized hydrogen condition using the ruthenium complex bearing an optically active 2,4-bis(diphenylphosphino)pentane (SKEWPHOS) and PICA as ligands, showing the results of 96% of conversion rate and 86% ee optical purity in only 2 hours under the condition of substrate concentration diluted at 0.1 mol/L, although a significant decrease in the optical purity is observed as compared to the same condition without pressurization of hydrogen (conversion rate 91%, optical purity 91% ee). In addition, when the substrate concentration was increased to 1.0 mol/L under pressurized hydrogen, 100% of conversion rate was reached after 17 hours, although the optical purity was markedly decreased to 39%, indicating that the addition of hydrogen did not effectively function. Moreover, said literature does not mention at all about that the optical purity of the generated alcohol would be improved by introducing a substituent onto PICA.

As an example of the use of a ruthenium complex bearing an optically active diphosphine and 2-picolylamine (PICA) as ligands for hydrogenation, the hydrogenation of tert-alkylketone using an ruthenium complex bearing an optically active diphosphine compound such as BINAP and 2-picolylamine has been reported (Patent Literature 4). However, the only diphosphine ligand exemplified in this literature is the diphosphine having an asymmetric structure to the axis such as BINAP. Said literature does not describe any reaction using as a catalyst a complex of diphosphine ligand having SKEWPHOS skeleton combined with 2-picolylamine, nor it refers to improving the optical purity of the generated alcohol by introducing a substituent onto PICA.

As an example of using a complex of diphosphine having SKEWPHOS skeleton with 2-picolylamine, the hydrogenation of 3-quinuclidinone (Patent Literature 5) and the hydrogenation of a heterocycle having a benzoyl group (Patent Literature 6) have been reported. However, the ketone substrates described in these literatures are only 3-quinuclidinone, 3-quinuclidinone having a substituent or a heterocycle having a benzoyl group, and there is no reference to reactions of simple ketones such as acetophenone. Furthermore, they do not refer to or suggest the likelihood of improving the optical purity of the generated alcohol compound by adding a substituent onto PICA.

As mentioned above, there has been no reports on an example wherein a ruthenium complex bearing a diphosphine having SKEWPHOS skeleton and a PICA ligand having more than one substituents on the pyridine ring or a ruthenium complex bearing as a ligand a heterocycle having more than one nitrogen atoms such as pyradine and pyrimidine effectively acts in the asymmetric hydrogenation of a carbonyl compound. Moreover, it has not been known the optical purity of the generated optically active alcohol can be improved as compared to using an unsubstituted PICA.

PRIOR ART LITERATURES

Patent Literatures

[Patent Literature 1] JP A 8-225466
[Patent Literature 2] JP A 11-189600
[Patent Literature 3] JP A 2007-536338
[Patent Literature 4] WO 2006/046508
[Patent Literature 5] WO 2006/103756
[Patent Literature 6] JP A 2011-51929

SUMMARY OF THE INVENTION

Problems to be Solved by the Invention

An object of the present invention is to provide a method for producing an optically active secondary alcohol in a high optical purity by hydrogenating a carbonyl compound at a high efficiency using as a catalyst a ruthenium complex bearing as ligands certain optically active diphosphine compound and a readily synthesized amine compound.

Means for Solving Problems

On the course of intensively investigating the hydrogenating reaction of a carbonyl compound as substrate, the inventors found that a ruthenium complex catalyst bearing an optically active SKEWPHOS (2,4-bis(diphenylphosphino) pentane) derivative compound, a readily-synthesized diphosphine compound having an asymmetric carbon atom, and a PICA-type ligand having more than one substituents on the pyridine ring or a PICA-type ligand in which the pyridine ring has been substituted with a heterocycle having more than one nitrogen atoms shows an excellent performance as a catalyst for asymmetric hydrogenation of a carbonyl compound, thereby completed the invention.

Namely, the invention relates to:

[1] A method for producing optically active secondary alcohols, wherein in the presence of one or more ruthenium complexes selected from the compound expressed by following general formula (1):

RuXYAB           (1)

[in the general formula (1),

X and Y are the same or different from each other and denote a hydrogen atom or an anionic group, A denotes an optically active diphosphine expressed by following general formula (2):

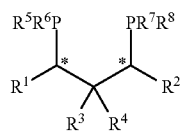

(in general formula (2), $R^1$ and $R^2$ are the same or different from each other, denote a C1-20 chained or cyclic hydrocarbon group which may have a substituent, $R^3$ and $R^4$ are the same or different from each other, denote hydrogen atoms or C1-3 hydrocarbon groups, $R^5$, $R^6$, $R^7$ and $R^8$ are the same or different from each other, denote hydrocarbon groups which may have a substituent,

* expresses an asymmetric carbon atom); and

B denotes an amine compound expressed by following general formula (3):

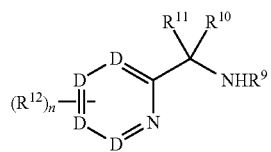

(in the general formula (3), each D is independently the same or different, denotes a carbon atom or nitrogen atom, $R^9$, $R^{10}$ and $R^{11}$ are the same or different from each other, a hydrogen atom or denote a C1-20 chained or cyclic hydrocarbon group which may have a substituent, and/or, $R^{10}$ and $R^{11}$ are connected to each other to form a saturated or unsaturated hydrocarbon ring or heterocycle which may have a substituent, each $R^{12}$ is the same or different from each other, denote a C1-20 chained or cyclic hydrocarbon group which may have a substituent, and/or, the adjacent $R^{12}$ are connected to each other to form a saturated or unsaturated hydrocarbon ring or heterocycle which may have a substituent, $R^{12}$ may at least partly be bound to ruthenium as an anionic group X, n is an integer of 0 to (4−(the number of D that are nitrogen atoms)), provided that n is an integer of 2 to 4 when the number of D that are nitrogen atoms is 0)], a substrate carbonyl compound (provided that 3-quinuclidinone, 3-quinuclidinone derivative having a substituent, and a ketone having an aromatic hydrocarbon group and a heterocycle are excluded) is reacted with hydrogen and/or a hydrogen donating compound.

[2] The method described in [1], wherein, in the reaction system, a ruthenium complex expressed by the general formula (1) is prepared in situ in the presence of:

one or more complexes selected from the compounds expressed by following general formula (4)

RuXYA           (4)

[in the general formula (4), X, Y and A each independently have the meaning as defined in the general formula (1)], and one or more amine compound selected from the compounds expressed by the above described general formula (3).

[3] The method described in [1] or [2], wherein n is 2 or more than 2.

[4] The method described in [3], wherein the adjacent $R^{12}$ are connected to each other to form a saturated or unsaturated hydrocarbon ring or heterocycle which may have a substituent, and a ring system formed by the ring formed by $R^{12}$ and a ring constituted by comprising D is a quinoline or isoquinoline ring system.

[5] The method described in any one of [1] to [4], wherein, in the general formula (3), one or more of four D are nitrogen atoms.

[6] The method described in any one of [1] to [5], wherein A is 2,4-bis(diphenylphosphino)pentane, 2,4-bis(di-4-tolylphosphino)pentane, 2,4-bis(di-3,5-xylylphosphino)pentane, 2,4-bis(di-4-tert-butylphenylphosphino)pentane, 2,4-bis(di-4-isopropylphenylphosphino)pentane, 2,4-bis(di-3,5-diethylphenylphosphino)pentane, 2,4-bis(di-3,5-diisopropylphenylphosphino)pentane, 2,4-bis(diphenylphosphino)-3-methylpentane, 2,4-bis(di-4-tolylphosphino)-3-methylpentane, 2,4-bis(di-3,5-xylylphosphino)-3-methylpentane, 2,4-bis(di-4-tert-butylphenylphosphino)-3-methylpentane, 2,4-bis(di-3,5-diethylphenylphosphino)-3-methylpentane, 2,4-bis(di-3,5-diisopropylphenylphosphino)-3-methylpentane, 1,3-bis(diphenylphosphino)-1,3-diphenylpropane, 1,3-bis(di-4-tolylphosphino)-1,3-diphenylpropane, 1,3-bis(di-3,5-xylylphosphino)-1,3-diphenylpropane, 1,3-bis(di-4-tert-butylphenylphosphino)-1,3-diphenylpropane, 1,3-bis(di-3,5-diethylphenylphosphino)-1,3-diphenylpropane, 1,3-bis (di-3,5-diisopropylphenylphosphino)-1,3-diphenylpropane, 1,3-bis(diphenylphosphino)-1,3-diphenyl-2-methylpropane, 1,3-bis(di-4-tolylphosphino)-1,3-diphenyl-2-methylpropane, 1,3-bis(di-3,5-xylylphosphino)-1,3-diphenyl-2-methylpropane, 1,3-bis(di-4-tert-butylphenylphosphino)-1,3-diphenyl-2-methylpropane, 1,3-bis(di-3,5-diethylphenylphosphino)-1,3-diphenyl-2-methylpropane or 1,3-bis(di-3,5-diisopropylphenylphosphino)-1,3-diphenyl-2-methylpropane.

[7] The method described in any one of [1] to [6], wherein A is 2,4-bis(diphenylphosphino)pentane, 2,4-bis(di-4-tolylphosphino)pentane, 2,4-bis(di-3,5-xylylphosphino)pentane, 2,4-bis(di-4-isopropylphenylphosphino)pentane, 2,4-bis(di-4-tert-butylphenylphosphino)pentane, 2,4-bis(di-3,5-diethylphenylphosphino)pentane or 2,4-bis (diphenylphosphino)-3-methylpentane.

[8] The method described in any one of [1] to [7], wherein B is 2-(aminomethyl)-3,4-dimethylpyridine, 2-(aminomethyl)-

3,5-dimethylpyridine, 2-(aminomethyl)-3,6-dimethylpyridine, 2-(aminomethyl)-4,5-dimethylpyridine, 2-(aminomethyl)-4,6-dimethylpyridine, 2-(aminomethyl)-5,6-dimethylpyridine, 2-(aminomethyl)-3,4,5-trimethylpyridine, 2-(aminomethyl)-3,5,6-trimethylpyridine, 2-(aminomethyl)-4,5,6-trimethylpyridine, 2-(aminomethyl)-3,4,5,6-tetramethylpyridine, 2-(aminomethyl)-3,4-diethylpyridine, 2-(aminomethyl)-3,5-diethylpyridine, 2-(aminomethyl)-3,6-diethylpyridine, 2-(aminomethyl)-4,5-diethylpyridine, 2-(aminomethyl)-4,6-diethylpyridine, 2-(aminomethyl)-5,6-diethylpyridine, 2-(aminomethyl)-3,4-di n-propylpyridine, 2-(aminomethyl)-3,5-di n-propylpyridine, 2-(aminomethyl)-3,6-di n-propylpyridine, 2-(aminomethyl)-4,5-di n-propylpyridine, 2-(aminomethyl)-4,6-di n-propylpyridine, 2-(aminomethyl)-5,6-di n-propylpyridine, 2-(aminomethyl)-3,4-diisopropylpyridine, 2-(aminomethyl)-3,5-diisopropylpyridine, 2-(aminomethyl)-3,6-diisopropylpyridine, 2-(aminomethyl)-4,5-diisopropylpyridine, 2-(aminomethyl)-4,6-diisopropylpyridine, 2-(aminomethyl)-5,6-diisopropylpyridine, 2-(aminomethyl)-3,4-di n-butylpyridine, 2-(aminomethyl)-3,5-di n-butylpyridine, 2-(aminomethyl)-3,6-di n-butylpyridine, 2-(aminomethyl)-4,5-di n-butylpyridine, 2-(aminomethyl)-4,6-di n-butylpyridine, 2-(aminomethyl)-5,6-di n-butylpyridine, 2-(aminomethyl)-3,4-diisobutylpyridine, 2-(aminomethyl)-3,5-diisobutylpyridine, 2-(aminomethyl)-3,6-diisobutylpyridine, 2-(aminomethyl)-4,5-diisobutylpyridine, 2-(aminomethyl)-4,6-diisobutylpyridine, 2-(aminomethyl)-5,6-diisobutylpyridine, 2-(aminomethyl)-3,4-di tert-butylpyridine, 2-(aminomethyl)-3,5-di tert-butylpyridine, 2-(aminomethyl)-3,6-di tert-butylpyridine, 2-(aminomethyl)-4,5-di tert-butylpyridine, 2-(aminomethyl)-4,6-di tert-butylpyridine, 2-(aminomethyl)-5,6-di tert-butylpyridine, 2-(aminomethyl)-3,4-diphenylpyridine, 2-(aminomethyl)-3,5-diphenylpyridine, 2-(aminomethyl)-3,6-diphenylpyridine, 2-(aminomethyl)-4,5-diphenylpyridine, 2-(aminomethyl)-4,6-diphenylpyridine, 2-(aminomethyl)-5,6-diphenylpyridine, 2-(aminomethyl)quinoline, 1-(aminomethyl)isoquinoline, 3-(aminomethyl)isoquinoline or 2-2-(aminomethyl)pyradine, 2-(aminomethyl)pyrimidine, 6-aminomethylphenanthridine, 2-(1-aminoethyl)-3,4-dimethylpyridine, 2-(1-aminoethyl)-3,5-dimethylpyridine, 2-(1-aminoethyl)-3,6-dimethylpyridine, 2-(1-aminoethyl)-4,5-dimethylpyridine, 2-(1-aminoethyl)-4,6-dimethylpyridine, 2-(1-aminoethyl)-5,6-dimethylpyridine, 2-(1-aminoethyl)-3,4,5-trimethylpyridine, 2-(1-aminoethyl)-3,5,6-trimethylpyridine, 2-(1-aminoethyl)-4,5,6-trimethylpyridine, 2-(1-aminoethyl)-3,4,5,6-tetramethylpyridine, 2-(1-aminoethyl)-3,4-diethylpyridine, 2-(1-aminoethyl)-3,5-diethylpyridine, 2-(1-aminoethyl)-3,6-diethylpyridine, 2-(1-aminoethyl)-4,5-diethylpyridine, 2-(1-aminoethyl)-4,6-diethylpyridine, 2-(1-aminoethyl)-5,6-diethylpyridine, 2-(1-aminoethyl)-3,4-di n-propylpyridine, 2-(1-aminoethyl)-3,5-di n-propylpyridine, 2-(1-aminoethyl)-3,6-di n-propylpyridine, 2-(1-aminoethyl)-4,5-di n-propylpyridine, 2-(1-aminoethyl)-4,6-di n-propylpyridine, 2-(1-aminoethyl)-5,6-di n-propylpyridine, 2-(1-aminoethyl)-3,4-diisopropylpyridine, 2-(1-aminoethyl)-3,5-diisopropylpyridine, 2-(1-aminoethyl)-3,6-diisopropylpyridine, 2-(1-aminoethyl)-4,5-diisopropylpyridine, 2-(1-aminoethyl)-4,6-diisopropylpyridine, 2-(1-aminoethyl)-5,6-diisopropylpyridine, 2-(1-aminoethyl)-3,4-di n-butylpyridine, 2-(1-aminoethyl)-3,5-di n-butylpyridine, 2-(1-aminoethyl)-3,6-di n-butylpyridine, 2-(1-aminoethyl)-4,5-di n-butylpyridine, 2-(1-aminoethyl)-4,6-di n-butylpyridine, 2-(1-aminoethyl)-5,6-di n-butylpyridine, 2-(1-aminoethyl)-3,4-diisobutylpyridine, 2-(1-aminoethyl)-3,5-diisobutylpyridine, 2-(1-aminoethyl)-3,6-diisobutylpyridine, 2-(1-aminoethyl)-4,5-diisobutylpyridine, 2-(1-aminoethyl)-4,6-diisobutylpyridine, 2-(1-aminoethyl)-5,6-diisobutylpyridine, 2-(1-aminoethyl)-3,4-di tert-butylpyridine, 2-(1-aminoethyl)-3,5-di tert-butylpyridine, 2-(1-aminoethyl)-3,6-di tert-butylpyridine, 2-(1-aminoethyl)-4,5-di tert-butylpyridine, 2-(1-aminoethyl)-4,6-di tert-butylpyridine, 2-(1-aminoethyl)-5,6-di tert-butylpyridine, 2-(1-aminoethyl)-3,4-diphenylpyridine, 2-(1-aminoethyl)-3,5-diphenylpyridine, 2-(1-aminoethyl)-3,6-diphenylpyridine, 2-(1-aminoethyl)-4,5-diphenylpyridine, 2-(1-aminoethyl)-4,6-diphenylpyridine, 2-(1-aminoethyl)-5,6-diphenylpyridine, 2-(1-aminoethyl)quinoline, 1-(1-aminoethyl)isoquinoline, 3-(1-aminoethyl)isoquinoline, 2-(1-aminoethyl)pyradine, 2-(1-aminoethyl)pyrimidine or 6-(1-aminoethyl)phenanthridine.

[9] A method for producing optically active secondary alcohols, characterized in that:

a substrate carbonyl compound (provided that 3-quinuclidinone, 3-quinuclidinone derivative having a substituent, and a ketone having an aromatic hydrocarbon group and a heterocycle are excluded) is reacted with hydrogen and/or a hydrogen donating compound in the presence of:

one or more complexes selected from the compounds expressed by following general formula (4):

RuXYA                                    (4)

[in the general formula (4),

X and Y are the same or different from each other, and denote a hydrogen or an anionic group, A denotes an optically active diphosphine expressed by following general formula (2):

(in the general formula (2), $R^1$ and $R^2$ are the same or different from each other, denote a C1-20 chained or cyclic hydrocarbon group which may have a substituent, $R^3$ and $R^4$ are the same or different from each other, denote a hydrogen atom or a C1-3 hydrocarbon group, $R^5$, $R^6$, $R^7$ and $R^8$ are the same or different from each other, denote a hydrocarbon group which may have a substituent,

* expresses an asymmetric carbon atom)], and one or more amine compounds selected from the compounds expressed by the following general formula (3):

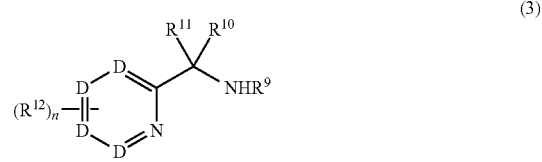

[In the general formula (3), each D is independently the same or different, denotes a carbon atom or nitrogen atom, $R^9$, $R^{10}$ and $R^{11}$ are the same or different from each other, denote a hydrogen atom or a C1-20 chained or cyclic hydrocarbon group which may have a substituent, and/or, $R^{10}$ and $R^{11}$ are connected to each other to form a saturated or unsaturated hydrocarbon ring or heterocycle which may have a substituent, each $R^{12}$ is the same or different from each other and denotes a C1-20 chained or cyclic hydrocarbon group which may have a substituent, and/or, the adjacent $R^{12}$ are connected to each other to form a saturated or unsaturated hydrocarbon ring or heterocycle which may have a substituent, $R^{12}$ may at least partly be bound to ruthenium as an anionic group X, n is an integer of 0 to (4−(the number of D that are nitrogen atoms)), provided that n is an integer of 2 to 4 when the number of D that are nitrogen atoms is 0].

[10] The production method described in any one of [1] to [9], wherein the substrate carbonyl compound is reacted with hydrogen.

[11] The production method described in any one of [1] to [10], wherein the substrate carbonyl compound is reacted with hydrogen in the presence of a base.

The Effects of the Invention

According to the present invention, a ruthenium complex catalyst acts as a highly efficient catalyst for hydrogenation, wherein said a ruthenium complex catalyst bearing an optically active SKEWPHOS (2,4-bis(diphenylphosphino)pentane) derivative compound which is a readily synthesized diphosphine compound having an asymmetric carbon, and a PICA-type ligand having more than one substituents on the pyridine ring or a PICA-type ligand substituted with a heterocycle in which the pyridine ring has more than one nitrogen atoms. This complex is inexpensive because it can employ as a ligand an achiral amine that can easily be synthesized instead of the optically active amine which has conventionally been employed. Such characteristic can be said to be industrially and economically preferential as compared to conventional methods. Moreover, an optically active secondary alcohol obtained by this method has a higher optical purity as compared to those obtained by an asymmetric hydrogenation or by an asymmetric reduction using a complex bearing conventional unsubstituted PICA as a ligand.

Embodiments for Practicing the Invention

Hereinbelow, the present invention is described in detail based on preferred embodiments.

The present invention is a method for producing an optically active secondary alcohol comprising reacting a substrate carbonyl compound (providing that the instances of 3-quinuclidinone, 3-quinuclidinone derivative having a substituent, and a ketone having an aromatic hydrocarbon group and a heterocycle are excluded) is reacted with hydrogen or a compound donating hydrogen in the presence of one or more ruthenium complexes selected from compounds expressed by the general formula (1) described below.

Hereinbelow, the ruthenium complex used in this method is described in detail and then suitable embodiments of such method are described in detail.

<Ruthenium Complex>

The ruthenium complex used in the present invention is expressed by a general formula (1):

RuXYAB    (1)

(wherein A is an optically active diphosphine compound A expressed by following general formula (2):

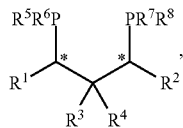

and B is an amine compound B expressed by following general formula (3):

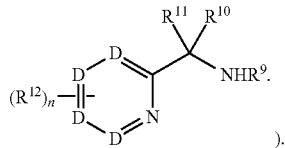

In general formula (1) mentioned above, substituents X and Y are the same or different from each other and denote a hydrogen atom or an anionic group.

As an anionic group, a halogen atom, carboxyl group, tetrahydroborate anion, and substituted phenyl anion group are suitable, though various other anionic groups, e.g., alkoxy group, hydroxy group and the like may be used. X and Y are preferably a hydrogen atom, a halogen atom, tetrahydroborate anion, an anionic tolyl group, acetoxy group, etc., more preferably a halogen atom or an anionic tolyl group, especially preferably, a chlorine atom or bromine atom.

Moreover, as mentioned above, the optically active diphosphine compound A in the optically active ruthenium complex expressed in the general formula (1) is expressed by following general formula (2):

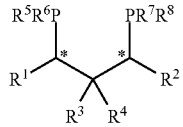

In the general formula (2), $R^1$ and $R^2$ are the same or different from each other and denote a C1-20 chained or cyclic hydrocarbon group which may have a substituent, $R^3$ and $R^4$ are the same or different from each other and denote hydrogen or a C1-3 hydrocarbon group, $R^5$, $R^6$, $R^7$ and $R^8$ are the same or different from each other and denote a hydrocarbon group which may have a substituent, and * denotes an asymmetric carbon atom.

Here, $R^1$ and $R^2$ include, without limitation, for example, a saturated or unsaturated chained aliphatic hydrocarbon group, a saturated or unsaturated, monocyclic or polycyclic, cyclic aliphatic hydrocarbon group, monocyclic or polycyclic aromatic hydrocarbon group and a combined group of these various hydrocarbon groups, etc., and these hydrocarbon groups may further have substituents.

Examples of $R^1$ and $R^2$ include hydrocarbon groups such as alkyl, alkenyl, cycloalkyl, cycloalkenyl, aryl, e.g., phenyl and naphthyl, aralkyl, e.g., phenylalkyl, as well as hydrocarbon groups in which said hydrocarbon groups further have an acceptable substituents such as alkyl, alkenyl, cycloalkyl, aryl, alkoxy, ester, acyloxy, a halogen atom, nitro group and cyano group.

Among these, $R^1$ and $R^2$ are preferably a saturated chained aliphatic hydrocarbon group or a monocyclic aromatic hydrocarbon group, more preferably, a methyl group, ethyl group, propyl group or a substituted or unsubstituted phenyl group, particularly preferably a methyl group and phenyl group.

$R^3$ and $R^4$ are a hydrogen atom or C1-3 hydrocarbon group, preferably an aliphatic saturated hydrocarbon group. In specific, a hydrogen atom, methyl group, ethyl group, propyl group, isopropyl group and the like are preferred.

$R^5$, $R^6$, $R^7$ and $R^8$ include, without limitation, for example, a saturated or unsaturated chained aliphatic hydrocarbon group, a saturated or unsaturated, monocyclic or polycyclic, cyclic aliphatic hydrocarbon group, a monocyclic or polycyclic aromatic hydrocarbon group and the like, and these hydrocarbon groups may further have substituents.

Examples of $R^5$, $R^6$, $R^7$ and $R^8$ include hydrocarbon groups such as alkyl, alkenyl, cycloalkyl, cycloalkenyl, aryl, e.g., phenyl and naphthyl, aralkyl, e.g., phenylalkyl as well as hydrocarbon groups in which said hydrocarbon groups further have an acceptable substituents such as alkyl, alkenyl, cycloalkyl, aryl, alkoxy, ester, acyloxy, a halogen atom, dialkyl amino group, nitro group and cyano group.

Among these, $R^5$, $R^6$, $R^7$ and $R^8$ are preferably a substituted or unsubstituted monocyclic aromatic hydrocarbon group, more preferably a phenyl group and substituted phenyl group, and especially preferably a phenyl group, as well as a substituted phenyl group that has at least one substituent selected from a methyl group, ethyl group, isopropyl group, propyl group and tert-butyl group.

The number of carbons in each of $R^5$, $R^6$, $R^7$ and $R^8$ may be, though not particularly limited to, for example, 1 to 20, preferably, 5 to 10.

Examples of the optically active diphosphine expressed by the general formula (2) include such as a pentane derivative having diphenylphosphino groups at 2- and 4-positions, a pentane derivative having di-4-tolylphosphino groups at 2- and 4-positions, a pentane derivative having di-4-t-butylphenylphosphino groups at 2- and 4-positions, a pentane derivative having di-3,5-xylylphosphino groups at 2- and 4-positions, a pentane derivative having di-3,5-diethylphenylphosphino groups at 2- and 4-positions, a 1,3-diphenylpropane derivative having diphenylphosphino groups at 1- and 3-positions, a 1,3-diphenylpropane derivative having di-4-tolylphosphino groups at 1- and 3-positions, a 1,3-diphenylpropane derivative having di-4-t-butylphenylphosphino groups at 1- and 3-positions, a 1,3-diphenylpropane derivative having di-3,5-xylylphosphino groups at 1- and 3-positions, a 1,3-diphenylpropane derivative having di-3,5-diethylphenylphosphino groups at 1- and 3-positions.

More specifically, the optically active diphosphine compound A is SKEWPHOS:2,4-bis(diphenylphosphino)pentane, TolSKEWPHOS:2,4-bis(di-4-tolylphosphino)pentane, XylSKEWPHOS:2,4-bis(di-3,5-xylylphosphino)pentane, 4-t-BuSKEWPHOS:2,4-bis(di-4-tert-butylphenylphosphino)pentane, 4-i-PrSKEWPHOS:2,4-bis(di-4-isopropylphenylphosphino)pentane, 3,5-diEtSKEWPHOS:2,4-bis(di-3,5-diethylphenylphosphino)pentane, 2,4-bis(di-3,5-diisopropylphenylphosphino)pentane, 2,4-bis(diphenylphosphino)-3-methylpentane, 2,4-bis(di-4-tolylphosphino)-3-methylpentane, 2,4-bis(di-3,5-xylylphosphino)-3-methylpentane, 2,4-bis(di-4-tert-butylphenylphosphino)-3-methylpentane, 2,4-bis(di-3,5-diethylphenylphosphino)-3-methylpentane, 2,4-bis(di-3,5-diisopropylphenylphosphino)-3-methylpentane, 1,3-bis(diphenylphosphino)-1,3-diphenylpropane, 1,3-bis(di-4-tolylphosphino)-1,3-diphenylpropane, 1,3-bis(di-3,5-xylylphosphino)-1,3-diphenylpropane, 1,3-bis(di-4-tert-butylphenylphosphino)-1,3-diphenylpropane, 1,3-bis(di-3,5-diethylphenylphosphino)-1,3-diphenylpropane, 1,3-bis(di-3,5-diisopropylphenylphosphino)-1,3-diphenylpropane, 1,3-bis(diphenylphosphino)-1,3-diphenyl-2-methylpropane, 1,3-bis(di-4-tolylphosphino)-1,3-diphenyl-2-methylpropane, 1,3-bis(di-3,5-xylylphosphino)-1,3-diphenyl-2-methylpropane, 1,3-bis(di-4-tert-butylphenylphosphino)-1,3-diphenyl-2-methylpropane, 1,3-bis(di-3,5-diethylphenylphosphino)-1,3-diphenyl-2-methylpropane or 1,3-bis(di-3,5-diisopropylphenylphosphino)-1,3-diphenyl-2-methylpropane.

The optically active diphosphine compound A is, more preferably, SKEWPHOS:2,4-bis(diphenylphosphino)pentane, TolSKEWPHOS:2,4-bis(di-4-tolylphosphino)pentane, XylSKEWPHOS:2,4-bis(di-3,5-xylylphosphino)pentane, 4-i-PrSKEWPHOS:2,4-bis(di-4-isopropylphenylphosphino)pentane, 4-t-BuSKEWPHOS:2,4-bis(di-4-tert-butylphenylphosphino)pentane, 4-i-PrSKEWPHOS:2,4-bis(di-4-isopropylphenylphosphino)pentane, 3,5-diEtSKEWPHOS:2,4-bis(di-3,5-diethylphenylphosphino)pentane, or 2,4-bis(diphenylphosphino)-3-methylpentane.

Among these, SKEWPHOS, TolSKEWPHOS, 3,5-diEtSKEWPHOS, t-BuSKEWPHOS, and XylSKEWPHOS are particularly suitable. However, naturally, the optically active diphosphine compounds that can be used in the present invention are by no means limited to these compounds.

Besides, as the amine compound B in the optically active ruthenium complex expressed by the general formula (1), a compound may be used which is expressed by following formula (3):

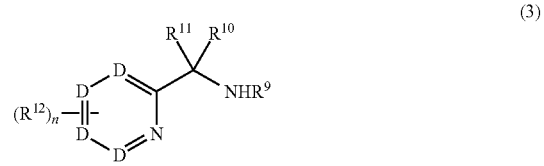

(3)

In the general formula (3), each D is independently the same or different, denotes a carbon atom or nitrogen atom, $R^9$, $R^{10}$ and $R^{11}$ are the same or different from each other, denote a hydrogen atom or a C1-20 chained or cyclic hydrocarbon group which may have a substituent, and/or $R^{10}$ and $R^{11}$ are connected to each other to form a saturated or unsaturated hydrocarbon ring or heterocycle which may have a substituent, each $R^{12}$ is the same or different from each other and denotes a C1-20 chained or cyclic hydrocarbon group which may have a substituent, and/or, the adjacent $R^{12}$ are connected to each other to form a saturated or unsaturated hydrocarbon ring or heterocycle which may have a substituent, $R^{12}$ may at least partly be bound to ruthenium as an anionic group X, n is an integer of 0 to (4−(the number of D that are nitrogen atoms)), provided that n is an integer of 2 to 4 when the number of D that are nitrogen atoms is 0.

Here, as mentioned above, in the formula each D is independently the same or different and denotes a nitrogen atom or carbon atom.

Nitrogen atoms which exist in the ring constituted by comprising D can be for example 1 to 3, preferably 1 to 2. Thus, in this case, of four D in the formula, 0 to 2, preferably, 0 or 1 D is nitrogen atom, and the other D are carbon atoms. In addition, when one or more of four D in the formula is (are)

nitrogen atom(s), the optical purity of the optically active secondary alcohol obtained in after-mentioned the method of the present invention will be high.

A ring constituted by comprising D can be, without limitation, for example, a pyridine ring, pyradine ring, pyrimidine ring, pyridazine ring, triazine ring or tetrazine ring. Among these, the ring constituted by comprising D is, preferably, a pyridine ring, pyradine ring or pyrimidine ring.

In the formula, $R^9$ to $R^{11}$ include, without limitation, for example, such as a hydrogen atom, a saturated or unsaturated chained aliphatic hydrocarbon group, a saturated or unsaturated, monocyclic or polycyclic, cyclic aliphatic hydrocarbon group, monocyclic or polycyclic aromatic hydrocarbon group, and these hydrocarbon groups may further have substituents.

Examples for $R^9$ to $R^{11}$ include a hydrogen atom, hydrocarbon groups such as an alkyl, alkenyl, cycloalkyl, cycloalkenyl, aryl, e.g., phenyl, naphthyl, aralkyl, e.g., phenylalkyl, as well as said hydrocarbon groups having various acceptable substituents such as an alkyl, alkenyl, cycloalkyl, aryl, alkoxy, ester, acyloxy, a halogen atom, nitro group or cyano group.

The above mentioned $R^9$ is preferably a hydrogen atom, alkyl group, phenyl group and phenylalkyl group, more preferably, a hydrogen atom, benzyl group, and particularly preferably a hydrogen atom.

The above mentioned $R^{10}$ and $R^{11}$ is preferably such as a hydrogen atom, alkyl group, phenyl group or phenylalkyl group, particularly preferably both are hydrogen atoms, or either $R^{10}$ or $R^{11}$ is a methyl group.

Moreover, $R^{10}$ and $R^{11}$ may be connected to each other to form a saturated or unsaturated hydrocarbon ring or heterocycle which may have a substituent. Such hydrocarbon ring includes a cycloalkane ring, cycloalkene ring or cycloalkyne ring having 3 to 10, preferably 4 to 8 ring members. Rings formed by $R^{10}$ and $R^{11}$ include, more specifically, e.g., cyclopropylidene, cyclobutylidene, cyclopentylidene, cyclohexylidene and pyperidylidene, either with or without further substituents. Among those described above, a monocyclic hydrocarbon group, in particular, cyclopentylidene and cyclohexylidene are preferred.

Furthermore, $R^{12}$ includes, without limitation, for example, such as a saturated or unsaturated chained aliphatic hydrocarbon group, a saturated or unsaturated, monocyclic or polycyclic, cyclic aliphatic hydrocarbon group, a monocyclic or polycyclic aromatic hydrocarbon group, and these hydrocarbon groups may further have substituents.

Examples for $R^{12}$ include hydrocarbon groups such as an alkyl, alkenyl, cycloalkyl, cycloalkenyl, aryl, e.g., phenyl, naphthyl, and aralkyl, e.g., phenylalkyl, as well as said hydrocarbon group having various acceptable substituents such as an alkyl, alkenyl, cycloalkyl, aryl, alkoxy, ester, acyloxy, a halogen atom, nitro group or cyano group.

The above mentioned $R^{12}$ is preferably an alkyl group or aryl group, more preferably a methyl group, ethyl group, isopropyl group, tert-butyl group, a substituted or unsubstituted phenyl group, especially preferably a methyl group, phenyl group, or o-, m- or p-tolyl group.

The adjacent $R^{12}$ may be connected to each other to form a saturated or unsaturated hydrocarbon ring or heterocycle that may have a substituent. A ring formed by $R^{12}$ includes a saturated or unsaturated hydrocarbon ring or heterocycle having 3 to 10, preferably 4 to 8 ring members, and more specifically, for example, a benzene ring, naphthalene ring, pyridine ring, pyradine ring, pyrimidine ring, pyridazine ring, triazine ring, tetrazine ring, imidazoline ring, pyrrole ring, imidazole ring, pyrazole ring, either with or without further substituents. Among those described above, a monocyclic hydrocarbon aromatic group, in particular benzene ring is preferred.

A ring system formed with a ring formed by $R^{12}$ and a ring constituted by comprising D includes, such as, for example, quinoline, isoquinoline, purine, quinoxaline, quinazoline, cinnoline, phthalazine, phenanthridine ring systems, and among these, quinoline or isoquinoline ring systems are preferred.

As mentioned above, in the formula, n is an integer of 0 to (4−(the number of D that are nitrogen atoms)), provided that n is an integer of 2 to 4 when the number of D that are nitrogen atoms is 0. Namely, n is from 2 to 4 when the number of D that are nitrogen atoms is 0; n is from 0 to 3 when the number of D that are nitrogen atoms is 1; n is from 0 to 2 when the number of D that are nitrogen atoms is 2; n is from 0 to 1 when the number of D that are nitrogen atoms is 3; and n is 0 when the number of D that are nitrogen atoms is 4. Furthermore, in the method discussed below according to the present invention, n is preferred to be 2 or higher such that an amine compound B has more than one substituents $R^{12}$ in order to obtain an optically active secondary alcohol at a high optical purity.

More specifically, an amine compound B preferably is, for example, 3,4-Me$_2$PICA:2-(aminomethyl)-3,4-dimethylpyridine, 3,5-Me$_2$PICA:2-(aminomethyl)-3,5-dimethylpyridine, 2-(aminomethyl)-3,6-dimethylpyridine, 2-(aminomethyl)-4,5-dimethylpyridine, 2-(aminomethyl)-4,6-dimethylpyridine, 2-(aminomethyl)-5,6-dimethylpyridine, 2-(aminomethyl)-3,4,5-trimethylpyridine, 2-(aminomethyl)-3,5,6-trimethylpyridine, 2-(aminomethyl)-4,5,6-trimethylpyridine, 2-(aminomethyl)-3,4,5,6-tetramethylpyridine, 2-(aminomethyl)-3,4-diethylpyridine, 2-(aminomethyl)-3,5-diethylpyridine, 2-(aminomethyl)-3,6-diethylpyridine, 2-(aminomethyl)-4,5-diethylpyridine, 2-(aminomethyl)-4,6-diethylpyridine, 2-(aminomethyl)-5,6-diethylpyridine, 2-(aminomethyl)-3,4-di n-propylpyridine, 2-(aminomethyl)-3,5-di n-propylpyridine, 2-(aminomethyl)-3,6-di n-propylpyridine, 2-(aminomethyl)-4,5-di n-propylpyridine, 2-(aminomethyl)-4,6-di n-propylpyridine, 2-(aminomethyl)-5,6-di n-propylpyridine, 2-(aminomethyl)-3,4-diisopropylpyridine, 2-(aminomethyl)-3,5-diisopropylpyridine, 2-(aminomethyl)-3,6-diisopropylpyridine, 2-(aminomethyl)-4,5-diisopropylpyridine, 2-(aminomethyl)-4,6-diisopropylpyridine, 2-(aminomethyl)-5,6-diisopropylpyridine, 2-(aminomethyl)-3,4-di n-butylpyridine, 2-(aminomethyl)-3,5-di n-butylpyridine, 2-(aminomethyl)-3,6-di n-butylpyridine, 2-(aminomethyl)-4,5-di n-butylpyridine, 2-(aminomethyl)-4,6-di n-butylpyridine, 2-(aminomethyl)-5,6-di n-butylpyridine, 2-(aminomethyl)-3,4-diisobutylpyridine, 2-(aminomethyl)-3,5-diisobutylpyridine, 2-(aminomethyl)-3,6-diisobutylpyridine, 2-(aminomethyl)-4,5-diisobutylpyridine, 2-(aminomethyl)-4,6-diisobutylpyridine, 2-(aminomethyl)-5,6-diisobutylpyridine, 2-(aminomethyl)-3,4-di tert-butylpyridine, 2-(aminomethyl)-3,5-di tert-butylpyridine, 2-(aminomethyl)-3,6-di tert-butylpyridine, 2-(aminomethyl)-4,5-di tert-butylpyridine, 2-(aminomethyl)-4,6-di tert-butylpyridine, 2-(aminomethyl)-5,6-di tert-butylpyridine, 2-(aminomethyl)-3,4-diphenylpyridine, 2-(aminomethyl)-3,5-diphenylpyridine, 2-(aminomethyl)-3,6-diphenylpyridine, 2-(aminomethyl)-4,5-diphenylpyridine, 2-(aminomethyl)-4,6-diphenylpyridine, 2-(aminomethyl)-5,6-diphenylpyridine, 2-AMQ:2-(aminomethyl)quinoline, 1-AMIQ:1-(aminomethyl)isoquinoline, 3-AMIQ:3-(aminomethyl)isoquinoline, 2-AMPZ:2-(aminomethyl)pyradine, 2-AMPR:2-(aminomethyl)pyrimidine, 6-(aminomethyl)phenanthridine, 2-(1-aminoethyl)-3,4-dimethylpyridine, 2-(1-aminoethyl)-3,5- dimethylpyridine, 2-(1-aminoethyl)-3,6-dimethylpyridine, 2-(1-aminoethyl)-4,5-dimethylpyridine, 2-(1-aminoethyl)-4,6-dimethylpyridine, 2-(1-aminoethyl)-5,6-dimethylpyridine, 2-(1-aminoethyl)-3,4,5-trimethylpyridine, 2-(1-aminoethyl)-3,5,6-trimethylpyridine, 2-(1-aminoethyl)-4,5,6-trimethylpyridine, 2-(1-aminoethyl)-3,4,5,6-tetramethylpyridine, 2-(1-aminoethyl)-3,4-diethylpyridine, 2-(1-aminoethyl)-3,5-diethylpyridine, 2-(1-aminoethyl)-3,6-diethylpyridine, 2-(1-aminoethyl)-4,5-diethylpyridine, 2-(1-aminoethyl)-4,6-diethylpyridine, 2-(1-aminoethyl)-5,6-diethylpyridine, 2-(1-aminoethyl)-3,4-di n-propylpyridine, 2-(1-aminoethyl)-3,5-di n-propylpyridine, 2-(1-aminoethyl)-3,6-di n-propylpyridine, 2-(1-aminoethyl)-4,5-di n-propylpyridine, 2-(1-aminoethyl)-4,6-di n-propylpyridine, 2-(1-aminoethyl)-5,6-di n-propylpyridine, 2-(1-aminoethyl)-3,4-diisopropylpyridine, 2-(1-aminoethyl)-3,5-diisopropylpyridine, 2-(1-aminoethyl)-3,6-diisopropylpyridine, 2-(1-aminoethyl)-4,5-diisopropylpyridine, 2-(1-aminoethyl)-4,6-diisopropylpyridine, 2-(1-aminoethyl)-5,6-diisopropylpyridine, 2-(1-aminoethyl)-3,4-di n-butylpyridine, 2-(1-aminoethyl)-3,5-di n-butylpyridine, 2-(1-aminoethyl)-3,6-di n-butylpyridine, 2-(1-aminoethyl)-4,5-di n-butylpyridine, 2-(1-aminoethyl)-4,6-di n-butylpyridine, 2-(1-aminoethyl)-5,6-di n-butylpyridine, 2-(1-aminoethyl)-3,4-diisobutylpyridine, 2-(1-aminoethyl)-3,5-diisobutylpyridine, 2-(1-aminoethyl)-3,6-diisobutylpyridine, 2-(1-aminoethyl)-4,5-diisobutylpyridine, 2-(1-aminoethyl)-4,6-diisobutylpyridine, 2-(1-aminoethyl)-5,6-diisobutylpyridine, 2-(1-aminoethyl)-3,4-di tert-butylpyridine, 2-(1-aminoethyl)-3,5-di tert-butylpyridine, 2-(1-aminoethyl)-3,6-di tert-butylpyridine, 2-(1-aminoethyl)-4,5-di tert-butylpyridine, 2-(1-aminoethyl)-4,6-di tert-butylpyridine, 2-(1-aminoethyl)-5,6-di tert-butylpyridine, 2-(1-aminoethyl)-3,4-diphenylpyridine, 2-(1-aminoethyl)-3,5-diphenylpyridine, 2-(1-aminoethyl)-3,6-diphenylpyridine, 2-(1-aminoethyl)-4,5-diphenylpyridine, 2-(1-aminoethyl)-4,6-diphenylpyridine, 2-(1-aminoethyl)-5,6-diphenylpyridine, 2-(1-aminoethyl)quinoline, 1-(1-aminoethyl)isoquinoline, 3-(1-aminoethyl)isoquinoline, 2-(1-aminoethyl)pyradine, 2-(1-aminoethyl)pyrimidine or 6-(1-aminoethyl)phenanthridine. Among these, in particular, 2-AMQ, 1-AMIQ, 3-AMIQ, 3,4-Me$_2$PICA, 3,5-Me$_2$PICA, 2-AMPZ, 2-AMPR are suitable.

The ruthenium complex expressed by the general formula (1) described hereinabove bears as an amine ligand an amine compound B expressed by the general formula (3), which either comprises more than one substituents on its contained nitrogen or comprises a nitrogen-containing ring with more than one nitrogen atoms. When a substrate carbonyl compound is hydrogenated using a ruthenium complex bearing such an amine compound B and an optically active diphosphine compound A expressed by the general formula (2), one can obtain an optically active secondary alcohol at much higher optical purity as compared to the case using a ruthenium complex bearing known conventional achiral ligand.

Moreover, the ruthenium complex expressed by the general formula (1) used in the present invention may also be prepared in the reaction system (in situ) upon reacting the substrate carbonyl compound with hydrogen in the presence of a base. Although such method is not limited, as an example, in the reaction system, the ruthenium complex expressed by the general formula (1) can be prepared in situ in the presence of one or more complexes selected from the precursor compound expressed by following general formula (4):

RuXYA (4)

[in the general formula (4), X, Y and A each independently have the meaning as defined in the general formula (1)]; and one or more amine compound selected from the compounds expressed by the above described general formula (3).

Molar ratio of a complex expressed by the general formula (4) and an amine compound expressed by the general formula (3) is not particularly limited. However, since the complex expressed by the general formula (4) and an amine compound expressed by the general formula (3) are reacted to generate a catalyst precursor expressed by the general formula (1), if the amount of the amine compound expressed by the general formula (3) is insufficient relative to that of the complex expressed by the general formula (4), the later remains without changing into the catalyst precursor expressed by the general formula (1), being disadvantageous from the viewpoint of reaction economy. Therefore, a complex expressed by the general formula (4) and an amine compound expressed by the general formula (3) may exist preferably at 1:1 to 1:50 molar ratio, more preferably at 1:1 to 1:20 molar ratio, in the vessel in which a substrate carbonyl compound will be reacted with hydrogen and/or a hydrogen donating compound. Even if the amount of the amine compound expressed by the general formula (3) is insufficient relative to that of the complex expressed by the general formula (4), they can be used without any problem, except that the reactivity would be reduced.

The ruthenium complex expressed by the general formula (1) or the general formula (4) may include one or more than one organic compound that is a reaction reagent used in its synthesis. Here, the organic compound denotes a coordinating organic compound exemplified by such as, for example, an aromatic hydrocarbon solvent such as toluene or xylene, an aliphatic hydrocarbon solvent such as pentane or hexane, a halogen-containing hydrocarbon solvent such as methylene dichloride, an ether solvent such as an ether or tetrahydrofuran, an alcoholic solvent such as methanol, ethanol, 2-propanol, butanol or benzyl alcohol, a ketone solvent such as acetone, methylethyl ketone and cyclohexyl ketone, a heteroatom-containing organic solvent such as acetonitrile, DMF, N-methylpyrrolidone, DMSO or triethylamine.

The synthesis of a ruthenium complex expressed by the general formula (1) can be carried out, as an example, by reacting an optically active ruthenium complex expressed by the general formula (4) with an amine compound or, alternatively, an optically active amine compound. The synthesis of an optically active ruthenium complex expressed by the general formula (4) can be carried out by reacting an optically active diphosphine compound with the source ruthenium complex. The complex expressed by the general formula (1) to be used may preliminarily be prepared as mentioned above, or may be prepared in situ during the reaction of hydrogenation. Any method that has been reported so far can be used for preparation of the ruthenium complex expressed by the general formula (1), including chemical structures of the source ingredients. Although not limited thereto, one of the embodiments is shown below.

A ruthenium complex as a starting material for synthesizing the complex that can be used may be a non-valent, monovalent, divalent or trivalent ruthenium complex, or those with higher valencies. When a non-valent or monovalent ruthenium complex is used, ruthenium needs to be oxidized by the final step. When a divalent complex is used, the synthesis can be carried out by reacting the ruthenium complex, an optically active diphosphine compound and optically active diamine compound in this order or in the reverse order, or by reacting these ingredients all together. When a trivalent ruthenium complex or a ruthenium complex of higher valency is used as the starting material, ruthenium needs to be reduced by the final step.

As a ruthenium complex to be starting material, an inorganic ruthenium compound such as ruthenium (III) chloride hydrate, ruthenium (III) bromide hydrate, ruthenium (III) iodide hydrate; a diene-coordinated ruthenium compound such as polynuclear [ruthenium(norbornadiene) bichloride], polynuclear [ruthenium(cycloocta-1,5-diene) bichloride] or bis(methyl allyl)ruthenium(cycloocta-1,5-diene); an aromatic compound-coordinated ruthenium complex such as polynuclear [ruthenium(benzene) bichloride], polynuclear [ruthenium(p-cymene) bichloride], polynuclear [ruthenium (trimethyl benzene) bichloride] or polynuclear [ruthenium (hexamethyl benzene) bichloride]; and a phosphine-coordinated complex such as dichlorotris(triphenyl phosphine) ruthenium, etc. may be employed. Any other ruthenium complexes may be used without limitation as long as it has a ligand which is capable of being substituted with an optically active diphosphine compound or an optically active diamine compound. For example, various ruthenium complexes described in COMPREHENSIVE ORGANOMETALLIC CHEMISTRY II (Vol. 7) p 294-296 (PERGAMON) can be used as a starting material.

When a trivalent ruthenium complex is used as a starting material, a phosphine-ruthenium halide complex can be synthesized by reacting, for example, a halogenated ruthenium (III) with excess amount of phosphine. Thus obtained phosphine-ruthenium halide complex with amine can then be reacted with amine to obtain the intended amine-phosphine-ruthenium halide complex expressed by the general formula (1). This type of synthesis is described, for example, in the literatures such as [J. Mol. Cat., 15, 297(1982)].

Namely, RuCl$_2$(PPh$_3$)$_3$ synthesized by a method such as those described in e.g., Inorg. Synth., vol 12, 237 (1970) is reacted in benzene with ethylenediamine to obtain RuCl$_2$ (PPh$_3$)$_2$(en) (note that there is no description about the yield). However, in this method, the reaction system is heterogeneous condition and tends to leave unreacted ingredients. On the other hand, the reaction can be carried out uniformly to improve the operability when the reaction solvent is changed to a solvent such as methylene dichloride or chloroform.

The reaction of a halogenated ruthenium and phosphine ligand can be carried out in a solvent such as: an aromatic hydrocarbon solvent such as toluene or xylene; an aliphatic hydrocarbon solvent such as pentane or hexane; a halogen-containing hydrocarbon solvent such as methylene dichloride; an ether solvent such as an ether or tetrahydrofuran; an alcoholic solvent such as methanol, ethanol, 2-propanol, butanol or benzyl alcohol; a heteroatom-containing organic solvent such as acetonitrile, DMF, N-methylpyrrolidone or DMSO, at a reaction temperature from −100° C. to 200° C. to give an phosphine-ruthenium halide complex expressed by the general formula (4).

The reaction of thus obtained phosphine-ruthenium halide complex expressed by the general formula (4) and an amine ligand expressed by the general formula (3) can be carried out in a solvent such as: an aromatic hydrocarbon solvent such as toluene or xylene; an aliphatic hydrocarbon solvent such as pentane or hexane; a halogen-containing hydrocarbon solvent such as methylene dichloride; an ether solvent such as an ether or tetrahydrofuran; an alcoholic solvent such as methanol, ethanol, 2-propanol, butanol or benzyl alcohol; a heteroatom-containing organic solvent such as acetonitrile, DMF, N-methylpyrrolidone or DMSO at a reaction temperature from −100° C. to 200° C. to give an amine-phosphine-ruthenium halide complex expressed by the general formula (1).

On the other hand, a divalent ruthenium complex may also be used from the beginning, reacting it with phosphine compound and amine compound in this order or in the reverse order. As an example, a diene-coordinated ruthenium compound such as polynuclear [ruthenium(norbornadiene) bichloride], polynuclear [ruthenium(cyclooct-1,5-diene) bichloride] or bis(methyl allyl)ruthenium(cyclooctadiene); an aromatic compound-coordinated ruthenium complex such as binuclear[ruthenium(benzene) bichloride], binuclear[ruthenium(p-cymene) bichloride], binuclear[ruthenium(trimethyl benzene) bichloride] or binuclear[ruthenium(hexamethyl benzene) bichloride]; or a phosphine-coordinated complex such as dichlorotris(triphenyl phosphine)ruthenium can be reacted with a phosphine compound in a solvent such as: an aromatic hydrocarbon solvent such as toluene or xylene; an aliphatic hydrocarbon solvent such as pentane or hexane; a halogen-containing hydrocarbon solvent such as methylene dichloride; an ether solvent such as an ether or tetrahydrofuran; an alcoholic solvent such as methanol, ethanol, 2-propanol, butanol or benzyl alcohol; or a heteroatom-containing organic solvent such as acetonitrile, DMF, N-methylpyrrolidone or DMSO at a reaction temperature from −100° C. to 200° C. to give a phosphine-ruthenium halide complex expressed by the general formula (4) or a phosphine-ruthenium methyl allyl complex. The phosphine-ruthenium methyl allyl complex can be reacted with hydrogen halide to give a phosphine-ruthenium halide complex.

The reaction of thus obtained phosphine-ruthenium halide complex expressed by the general formula (4) with a diamine compound can be carried out by reacting it with amine ligand in an organic solvent such as: an aromatic hydrocarbon solvent such as toluene or xylene; an aliphatic hydrocarbon solvent such as pentane or hexane; a halogen-containing hydrocarbon solvent such as methylene dichloride; an ether solvent such as an ether or tetrahydrofuran; an alcoholic solvent such as methanol, ethanol, 2-propanenol, butanol or benzyl alcohol; or a heteroatom-containing organic solvent such as acetonitrile, DMF, N-methylpyrrolidone or DMSO, at a reaction temperature from −100° C. to 200° C. to give an amine-phosphine-ruthenium complex. Also, in a similar condition, a cationic ruthenium complex such as [chlororuthenium(BINAP)(benzene)]chloride can be reacted with an amine ligand to give an amine-phosphine-ruthenium halide complex expressed by the general formula (1).

A complex in which a cyclic hydrocarbon group bound to a diamine compound expressed by the general formula (3) (an anionic group X) is bound to ruthenium can be synthesized by a method described in the literatures such as [Organometallics, 29, 3563(2010)]. Namely, similar to the synthesis method of the above mentioned amine-phosphine-ruthenium halide complex, an amine ligand is added to a phosphine-ruthenium halide complex expressed by the general formula (4) to synthesize an amine-phosphine-ruthenium halide complex, and this is then reacted with a base such as triethylamine in a solvent such as: an aromatic hydrocarbon solvent such as toluene or xylene; an aliphatic hydrocarbon solvent such as pentane or hexane; a halogen-containing hydrocarbon solvent such as methylene dichloride; an ether solvent such as an ether or tetrahydrofuran; an alcoholic solvent such as methanol, ethanol, 2-propanenol, butanol or benzyl alcohol; or a heteroatom-containing organic solvent such as acetonitrile, DMF, N-methylpyrrolidone or DMSO, at temperature from −100° C. to 200° C. Alternatively, it can be synthesized by reacting the phosphine-ruthenium halide complex expressed by the general formula (4) with the amine ligand in above mentioned solvent in the presence of a base such as triethylamine at temperature from −100° C. to 200° C.

Although the synthesized amine-phosphine-ruthenium halide complex expressed by the general formula (1) may be a mixture of several complexes with different coordination manner, it can directly be used for the hydrogenating reaction without purifying to obtain single structure complex.

<Method of Producing an Optically Active Secondary Alcohol>

Next, the method of producing an optically active secondary alcohol according to this embodiment will be explained.

the method of producing an optically active secondary alcohol according to this embodiment is to react a substrate carbonyl compound (provided that 3-quinuclidinone, 3-quinuclidinone derivative having a substituent, and a ketone having an aromatic hydrocarbon group and a heterocycle are excluded) with hydrogen and/or a hydrogen donating compound in the presence of one or more ruthenium complexes expressed by the above mentioned general formula (1).

The ruthenium complex is that functions as a catalyst in the present method. The ruthenium complex can be any one of those expressed by the above-mentioned general formula (1), though by selecting either (R,R) isomer or (S,S) isomer from the optically active diphosphine compound expressed by the general formula (2), the optically active secondary alcohol of desired absolute configuration can selectively be prepared.

When the amine compound expressed by the general formula (3) in the ruthenium complex expressed by the general formula (1) is optically active, the combination of the absolute structure of the diphosphine compound in the optically active ruthenium complex expressed by the general formula (4) and the absolute structure of the optically active amine compound to be added is important for obtaining a high optical purity. Moreover, an appropriate combination of the absolute structure of the diphosphine compound and the absolute structure of the amine compound will vary depending on, e.g., the structure of the substrate. The use of a complex with an inappropriate combination might decrease the catalytic activity or decrease the optical purity of the product as compared to the case when a complex with an appropriate combination is used.

The amount of the ruthenium complex expressed by the general formula (1) varies depending on the conditions or economies of the reaction such as the reaction vessel to be used, hydrogen purity, types and purities of the solvents to be used, or the purity of the substrate, though it can be used in a range of 1/100 to 1/10,000,000 in molar ratio, preferably in a range of 1/500 to 1/1,000,000 in molar ratio to the substrate carbonyl compound.

As the substrate carbonyl compounds, any one or more in combination carbonyl compounds can be used except 3-quinuclidinone, 3-quinuclidinone derivative having a substituent, and a ketone having an aromatic hydrocarbon group and a heterocycle.

The carbonyl compounds which can be used are not particularly limited, though aromatic ketones and heteroaromatic ketones, and these ketones in which the aromatic ring or heterocycle has a substituent, i.e., compounds in which a hydrogen atom in the aromatic ring has been substituted with a carbonyl group, and said compound in which any hydrogen atom has been substituted with any substituent are effective.

The aromatic ring in such an aromatic ketone is not particularly limited, and may be monocyclic or polycyclic, and includes such as, for example, a benzene ring, naphthalene ring, azulene ring, acenaphthylene ring, anthracene ring, fluorene ring, phenanthrene ring, biphenylene ring, pyrene ring, tetracene ring, and among these, a benzene ring and a naphthalene ring are preferred.

The heterocycle in a heteroaromatic ketone is not particularly limited, includes, e.g., a monocyclic or polycyclic heterocycle having a nitrogen atom, oxygen atom or sulfur atom as a heteroatom, specifically such as a pyridine ring, pyradine ring, pyrimidine ring, pyridazine ring, triazine ring, tetrazine ring, imidazoline ring, pyrrole ring, imidazole ring, pyrazole ring, quinoline ring, isoquinoline ring, purine ring, quinoxaline ring, quinazoline ring, cinnoline ring, phthalazine ring, phenanthridine ring, furan ring, oxazole ring, isooxazole ring, thiophene ring, thiazole ring, isothiazole ring, and among these, a pyridine ring, pyradine ring, pyrimidine ring, furan ring and thiophene ring are preferred.

A substituent on the aromatic ring or heteroaromatic ring includes, e.g., an alkyl, alkenyl, cycloalkyl, aryl, alkoxy, ester, a halogen atom, amino group, amido group, nitro group and cyano group.

A group which directly is bound to the carbonyl group other than aromatic ring or heteroaromatic ring includes an ester group, or a hydrocarbon group such as an alkyl, alkenyl, cycloalkyl, cycloalkenyl and aralkyl, and these hydrocarbon group further having various acceptable substituents such as an alkyl group, alkenyl group, cycloalkyl group, aryl group, aralkyl group, alkoxy group, ester, a halogen atom, amino group, amido group, nitro group and cyano group.

Among these ketones, in particular, the present invention is effective on the reaction of aromatic ketones with high steric hindrance, or heteroaromatic ketones with high steric hindrance.

Specific examples of particularly effective carbonyl compounds include: 2'-fluoroacetophenone, 2'-chloroacetophenone, 2'-bromoacetophenone, 2'-iodoacetophenone, 2'-methylacetophenone, 2'-ethylacetophenone, 2'-isopropylacetophenone, 2'-methoxyacetophenone, 3-fluoro-4-acetylpyridine, 3-chloro-4-acetylpyridine, 3-bromo-4-acetylpyridine, 3-iodo-4-acetylpyridine, 3-methyl-4-acetylpyridine, 3-ethyl-4-acetylpyridine, 3-isopropyl-4-acetylpyridine, 2-fluoro-3-acetylpyridine, 2-chloro-3-acetylpyridine, 2-bromo-3-acetylpyridine, 2-iodo-3-acetylpyridine, 2-methyl-3-acetylpyridine, 2-ethyl-3-acetylpyridine, 2-isopropyl-3-acetylpyridine, 4-fluoro-3-acetylpyridine, 4-chloro-3-acetylpyridine, 4-bromo-3-acetylpyridine, 4-iodo-3-acetylpyridine, 4-methyl-3-acetylpyridine, 4-ethyl-3-acetylpyridine, 4-isopropyl-3-acetylpyridine, 2-fluoro-3-acetylfuran, 2-chloro-3-acetylfuran, 2-bromo-3-acetylfuran, 2-iodo-3-acetylfuran, 2-methyl-3-acetylfuran, 2-ethyl-3-acetylfuran, 2-isopropyl-3-acetylfuran, 2-fluoro-3-acetylthiophene, 2-chloro-3-acetylthiophene, 2-bromo-3-acetylthiophene, 2-iodo-3-acetylthiophene, 2-methyl-3-acetylthiophene, 2-ethyl-3-acetylthiophene, 2-isopropyl-3-acetylthiophene, 2',6'-difluoroacetophenone, 2',6'-dichloroacetophenone, 2',6'-bromoacetophenone, 2',6'-iodoacetophenone, 2',6'-dimethylacetophenone, 2',6'-diethylacetophenone, 2',6'-diisopropylacetophenone, 2',6'-dimethoxyacetophenone, 3,5-difluoro-4-acetylpyridine, 3,5-dichloro-4-acetylpyridine, 3,5-dibromo-4-acetylpyridine, 3,5-diiodo-4-acetylpyridine, 3,5-dimethyl-4-acetylpyridine, 3,5-diethyl-4-acetylpyridine, 3,5-diisopropyl-4-acetylpyridine, 2,4-difluoro-3-acetylpyridine, 2,4-dichloro-3-acetylpyridine, 2,4-dibromo-3-acetylpyridine, 2,4-diiodo-3-acetylpyridine, 2,4-dimethyl-3-acetylpyridine, 2,4-diethyl-3-acetylpyridine, 2,4-diisopropyl-3-acetylpyridine, 2,4-difluoro-3-acetylfuran, 2,4-dichloro-3-acetylfuran, 2,4-dibromo-3-acetylfuran, 2,4-diiodo-3-acetylfuran, 2,4-dimethyl-3-acetylfuran, 2,4-diethyl-3-acetylfuran, 2,4-diisopropyl-3-acetylfuran, 2,4-difluoro-3-acetylthiophene, 2,4-dichloro-3-acetylthiophene, 2,4-dibromo-3-acetylthiophene, 2,4-diiodo-3-acetylthiophene, 2,4-dimethyl-3-acetylthiophene, 2,4-diethyl-3-acetylthiophene, 2,4-diisopropyl-3-acetylthiophene, 2',6'-dichloro-3'-fluoroacetophenone, 2',4',6'-trimethylacetophenone, 2',4',6'-trimethoxyacetophenone and 2',6'-bis(trifluoromethyl)acetophenone. Furthermore, the carbonyl compounds exemplified here may further have aforementioned substituents.

The aforementioned 3-quinuclidinone derivative having a substituent is 3-quinuclidinone in which one or more hydrogen atoms thereof have been substituted with any substituents. Namely, 3-quinuclidinone derivative having a substituent is any compound having a 3-quinuclidinone skeleton.

Moreover, the ketone having an aromatic hydrocarbon group and a heterocycle is a ketone described by following general formula (5):

$$Ar^1-C(=O)-Ar^2 \quad (5)$$

(wherein $Ar^1$ comprises at least one nitrogen atom, sulfur atom or oxygen atom within the ring, and these heteroatoms is an aromatic heterocycle group with 6 to 7 members which may form a salt, $Ar^2$ is an aromatic hydrocarbon group that may have 0 to 10 C1-20 alkyl groups, alkoxy groups, hydroxy alkyl groups, halogen groups, amino groups, ester groups, amido groups, nitro groups and cyano groups which may be the same or different).

As hydrogen source used in the inventive method, hydrogen (hydrogen gas) and/or a hydrogen-donating compound (hydrogen donor) can be used as described above.

The hydrogen donor herein refers to a compound that act to provide the ruthenium catalyst with hydrogen within the molecule, and such compound includes, without limitation, e.g., lower alcohols such as 2-propanol, propanol, butanol, ethanol and methanol, as well as formic acid and formate salts such as potassium formate and sodium formate.

Among those described above, lower alcohol is preferably used as the hydrogen donor, and more preferably 2-propanol is used.

The hydrogen donor may be used, without limitation, in a range from 1 to 20 eq. relative to that of the substrate carbonyl compound, preferably, in the range from 1 to 10 eq.

Moreover, as hydrogen source, it is preferred to use hydrogen gas in the view that a sufficient reactivity can be obtained.

When hydrogen gas is used, the pressure of the hydrogen gas is not particularly limited, though, it is for example in a range from 1 to 200 atm, preferably in a range from 1 to 100 atm, particularly preferably in a range from 1 to 20 atm.

Furthermore, hydrogen gas and hydrogen donor can be used in combination.

It is preferable that a base is present in the reaction system. The bases which may be used includes, without limitation, for example, salts of alkaline metal or alkaline earth metal salts such as KOH, KOCH$_3$, KOCH(CH$_3$)$_2$, KOC(CH$_3$)$_3$, KC$_{10}$H$_8$, LiOH, LiOCH$_3$, LiOCH(CH$_3$)$_2$, LiOC(CH$_3$)$_3$ and quaternary ammonium salts, and one or more from these may be used in combination. Among these, the base preferably is KOH or KOCH(CH$_3$)$_2$, and particularly preferably KOCH(CH$_3$)$_2$.

The amount of base to be added is, without limitation, for example, an amount such that the base concentration will be 0.001 to 0.2 moles/L in the reaction system, preferably an amount such that the base concentration will be 0.005 to 0.1 moles/L, more preferably an amount such that the base concentration will be 0.01 to 0.05 moles/L.

As discussed above, the ruthenium complex indicated by the general formula (1) to be used as the catalyst and the base are essential ingredients in order to smoothly conduct the reaction of asymmetric hydrogenation to achieve a high asymmetric yield, and the reaction activity will not be sufficient to obtain an optically active alcohol at a high optical purity if either one ingredient is insufficient.

However, when X and Y in the ruthenium complex expressed by the general formula (1) are hydrogen atoms, or alternatively when X is a hydrogen atom and Y is tetrahydroborate anion, the ruthenium complex and substrate carbonyl compound may be mixed and then, without adding a base, the reaction may be conducted by applying pressurized hydrogen and stirring. In such case, still the substrate carbonyl compound may be hydrogenated.

A solvent may also be present in the reaction system.

The solvents which can be used are not particularly limited, but those which solubilize the substrate and the catalyst system are preferred. Examples include lower alcohols such as methanol, ethanol, n-propanol, 2-propanol, butanol and benzyl alcohol; aliphatic hydrocarbon solvents such as pentane and hexane; halogen-containing hydrocarbon solvents such as methylene dichloride; ether solvents such as ether, methyl-tert-butyl ether, cyclopentylmethyl ether and tetrahydrofuran; and heteroatom-containing organic solvents such as acetonitrile, N,N-dimethylformamide (DMF), N-methylpyrrolidone and dimethylsulfoxide (DMSO), and one or more from these may be used in combination.

The amount of the solvent is determined according to the solubilities of the reaction substrates and economies. For instance, although some substrates can be reacted at low concentration of 0.1 moles/L or below in the reaction system to almost without solvent depending on the types of the substrates, it is preferred to use the substrate at the concentration in a range from 0.3 to 5 moles/L.

The higher limit of the reaction temperature is needed to be set in a range such that the decomposition of the catalytic ruthenium complex will not occur, and the lower limit is needed to be set in consideration of the activity. For instance, the reaction is preferably carried out at 0 to 60° C., preferably at 25 to 40° C., and such temperature range can be considered good from economic point of view.

The reaction time varies depending on the reaction condition such as the reaction solvent, the concentration of the reaction substrate, the temperature, the pressure and the substrate/catalyst ratio, though it can optionally be set from several minutes to several dozen hours, e.g., 10 minutes to 96 hours, preferably 2 hours to 48 hours such that the reaction will be completed within that time, in consideration of the ease of reaction operation and economic efficiency.

In addition, no problem will be observed even if the reaction operation is continuously carried on after the completion of the reduction of the carbonyl groups of the substrate. Therefore, upon carrying out the present invention, there is no need to constantly monitor the progress of the reaction, nor any need to stop the reaction immediately after the completion of the reaction. Accordingly, the reaction time may be set longer than the substantial reaction time, providing the method with an advantage in industrial practice.

By hydrogenating substrate carbonyl compounds according to the method described above, corresponding optically active alcohols can be obtained.

However, even by the method of the present invention, the product of the hydrogenating reaction might contain the source material ketone, added base or a salt generated by the reaction of the complex and the base. These can be removed by generally known purification operation such as distillation, washing, recrystallization and chromatography.

The reaction manner of the above mentioned reaction is not particularly limited and the reaction can be carried out in any of a batch method, a continuous method or in a micro-flow reactor.

According to the present invention as discussed above, a readily synthesized diphosphine compound having an asymmetric carbon, i.e., an optically active SKEWPHOS (2,4-bis(diphenylphosphino)pentane) derivative compound, and a ruthenium complex catalyst bearing a PICA-type ligand having more than one substituents on the pyridine ring or a PICA-type ligand substituted with a heterocycle in which the pyridine ring has more than one nitrogen atoms act as a hydrogenating catalyst with a high efficiency. This complex is not the optically active amine which has conventionally been employed, and inexpensive because it can employ a readily synthesized achiral amine as a ligand. Such characteristics can be considered industrially and economically excellent as compared to conventional methods. In addition, the optically active secondary alcohol obtained by the method of the present invention has a higher optical purity than that obtained by a conventional method.

According to another embodiment of the present invention, the method of producing an optically active secondary alcohols is characterized in that a substrate carbonyl compound (provided that 3-quinuclidinone, 3-quinuclidinone derivative having a substituent, and a ketone having an aromatic hydrocarbon group and a heterocycle are excluded) is reacted with hydrogen and/or a hydrogen donating compound in the presence of:

one or more complexes selected from the compounds expressed by following general formula (4):

RuXYA                                    (4)

[in the general formula (4), X and Y are the same or different from each other and have the meaning as defined in the general formula (1)], and one or more amine compounds expressed by the above mentioned general formula (3).

The complex expressed by the general formula (4) and the amine compound expressed by the general formula (3) may be placed preferably at a molar ratio from 1:1 to 1:50, more preferably at a molar ratio from 1:1 to 1:20 in a vessel in which the substrate carbonyl compound is reacted with hydrogen and/or a hydrogen donating compound.

The aforementioned other conditions can be used in this embodiment.

A similar result can be obtained by a method according to such embodiment.

WORKING EXAMPLES

Hereinafter, the present invention will be further explained in detail by the way of Working Examples, although the present invention is not to be limited by following Working Examples. In following Working Examples, all reactions were carried out under an inert gas atmosphere such as argon gas or nitrogen gas. The solvent used in the reaction had been dehydrated and degassed unless otherwise described. The hydrogenating reaction of the carbonyl compound was carried out in an autoclave with pressurized hydrogen.

The ketone substrates described in Working Examples and Comparative Examples were purchased as reagents and directly used, unless otherwise described. The solvents used in the reactions were the dehydrated solvent from KANTO CHEMICAL CO., INC., which were directly used. Other chemicals were the reagents from KANTO CHEMICAL CO., INC. which were directly used, unless otherwise described.

In Working Examples and Comparative Examples described below, S/C denotes the substrate/catalyst molar ratio.

Following apparatuses were used for measurement below:
NMR: JNM-ECX400P (400 MHz) (JEOL Ltd.)
Internal standard substance: $^1$H-NMR tetramethylsilane
External standard substance: $^{31}$P-NMR 85% phosphoric acid
The optical purity measurement by GC
Measuring apparatus: GC-17A (FID detector, Simadzu Corporation)
Column: CP Chirasil-DEX CB (0.25 mml. D×25 m, DF=0.25 µm) (from VARIAN)
The optical purity measurement by HPLC
Measuring apparatus: LC-20A (UV detector, Simadzu Corporation)
Column: CHIRALPAK AD-RH (4.6 mmφ×150 mm) (DAICEL Corporation)

1. Synthesis of Ruthenium Complexes

Synthetic Examples 1 to 6

Syntheses of Various PICA-Type Amine Ligands

A synthetic method for 2-aminomethyl-3,4-dimethylpyridine (3,4-Me$_2$PICA) is described below as an example.

Firstly, under an argon gas atmosphere, 27.3 g of 3,4-dimethylpyridine (Aldrich) (255 mmol) in 150 mL acetic acid solution was cooled on ice, and 25 mL of 35% hydrogen peroxide aqueous solution was added thereto, stirred at 75° C. for 3 hours. Then additional 17.5 mL of 35% hydrogen peroxide aqueous solution was added and stirred at 75° C. for 3 hours. The reaction solution was neutralized by adding an aqueous solution of sodium hydrogen carbonate, extracted with methylene dichloride. The extract was dried on salt cake and concentrated to give a solid. The obtained solid was washed with ethyl acetate to give 29.55 g of 3,4-dimethylpyridine-N-oxide (94% yield).

17.8 g of the obtained 3,4-dimethylpyridine-N-oxide (144.5 mmol) was dissolved under an argon gas atmosphere in 250 mL of methylene dichloride, added thereto 13.2 mL of dimethyl carbamoyl chloride (144 mmol), then 19.0 mL of trimethylsilyl cyanide (152 mmol), and stirred overnight at room temperature. The reaction solution was quenched with 10%-K$_2$CO$_3$ aqueous solution, the methylene dichloride layer was separated, dried on salt cake and concentrated to give 3.40 g of 6-cyano-3,4-dimethylpyridine (18% yield).

In an autoclave, 3.40 g of 6-cyano-3,4-dimethylpyridine (25.7 mmol), 0.15 g of Pd/C (water-content=50%), 200 mL methanol and 3.0 mL concentrated hydrochloric acid are placed, stirred at room temperature for 3 hours while pressurizing with hydrogen to 3 atm. The reaction solution was filtered through Celite and the filtrate was concentrated to dryness. This was washed with methanol to give 2.41 g of 2-aminomethyl-3,4-dimethylpyridine (3,4-Me$_2$PICA) hydrochloride (93% yield). This 2-aminomethyl-3,4-dimethylpyridine hydrochloride was treated with an aqueous solution of potassium carbonate to give 2-aminomethyl-3,4-dimethylpyridine (3,4-Me$_2$PICA) quantitatively.

2-aminomethyl-3,5-dimethylpyridine (3,5-Me$_2$PICA) was synthesized in a similar way. As for 1-aminomethyl isoquinoline (1-AMIQ), 3-aminomethyl isoquinoline (3-AMIQ), 2-aminomethyl quinoline (2-AMQ) and 2-aminomethyl pyrimidine (2-AMPR), corresponding nitrile intermediates are in market from Sigma-Aldrich Co. LLC. and these were used as source materials.

The yields of the synthesized compounds, etc., are summarized in the Table below.

TABLE 1

| | Substituted pyridine | N-oxide intermediate | Nitrile intermediate | Synthesized compound | 1H-NMR spectrum (399.78 MHz, CD3OD) |
|---|---|---|---|---|---|
| Synthetic Example 1 | 3,4-dimethylpyridine source material | 3,4-dimethylpyridine N-oxide 94% yield | 2-cyano-3,4-dimethylpyridine 18% yield | 2-aminomethyl-3,4-dimethylpyridine 93% yield | δ 8.18 ppm (d, 1H), 7.09 (d, 1H), 3.90 (s, 2H), 2.32 (s, 3H), 2.25 (s, 3H) |
| Synthetic Example 2 | 3,5-dimethylpyridine source material | 3,5-dimethylpyridine N-oxide 62% yield | 2-cyano-3,5-dimethylpyridine 47% yield | 2-aminomethyl-3,5-dimethylpyridine 25% yield | δ 8.16 ppm (s, 1H), 7.41 (s, 1H), 3.84 (s, 2H), 2.30 (s, 3H), 2.28 (s, 3H) |
| Synthetic Example 3 | | | 1-cyanoisoquinoline source material | 1-aminomethylisoquinoline 43% yield | δ 8.39 ppm (d, 1H), 8.23 (s, 1H), 7.92 (s, 1H), 7.77-7.66 (m, 3H), 4.42 (s, 2H) |
| Synthetic Example 4 | | | 3-cyanoisoquinoline source material | 3-aminomethylisoquinoline 21% yield | δ 9.23 ppm (s, 1H), 8.06 (d, 1H), 7.90 (d, 1H), 7.78-7.74 (m, 2H), 7.68 (s, 1H), 4.03 (s, 2H) |
| Synthetic Example 5 | | | 2-cyanoquinoline source material | 2-aminomethylquinoline 21% yield | δ 8.29 ppm (d, 1H), 8.00 (s, 1H), 7.89 (s, 1H), 7.73 (m, 1H), 7.56 (m, 2H) 4.07 (s, 2H) |
| Synthetic Example 6 | | | 2-cyanopyrimidine source material | 2-aminomethylpyrimidine 29% yield | δ 8.75 ppm (d, 2H), 7.35 (t, 1H), 7.90 (d, 1H), 4.00 (s, 2H) |

Synthetic Example 7

The synthesis of 2-aminomethyl pyradine (2-AMPZ)

The synthesis of 2-aminomethyl pyradine (2-AMPZ) was carried out by a method shown below, by reference to the method described in literature (JP A 2001-894594). 2-cyanopyradine used was from Sigma-Aldrich Co. LLC.

1.05 g of 2-cyanopyradine (10 mmol) and 100 mg of 60 wt %-Ni/SiO₂ were placed in an autoclave (SUS316) with 20 mL of toluene and replaced with argon gas. This was pressurized with hydrogen gas to 50 atm, stirred at 140° C. for 4 hours. The reaction solution was filtered and concentrated to give 2-aminomethyl pyradine (2-AMPZ) quantitatively.

1H-NMR spectrum (399.78 MHz, CDCl₃):δ8.60-8.45 (m, 3H), 4.07 (s, 2H), 1.79 (br, 2H)

Synthetic Example 8

Synthetic Example of RuBr₂[(S,S)-xylskewphos](3,4-Me₂ pica)

(1) The synthesis of RuBr₂[(S,S)-xylskewphos](methyl allyl)₂

To an argon-replaced 50 mL Schlenk tube (S,S)-xyl-SKEWPHOS (110 mg, 0.2 mol) and Ru(cycloocta-1,5-diene)(methyl allyl)₂ (64 mg, 0.2 mmol) were placed. Then 5 mL of hexane was added and stirred at 70° C. for 6 hours. Insoluble matter was filtered off through a glass filter, the filtrate was concentrated to give the intended material. This was used for the next reaction without purification in particular.

(2) The synthesis of RuBr$_2$[(S,S)-xylskewphos]

RuBr$_2$[(S,S)-xylskewphos] (methyl allyl)$_2$ complex (153 mg, 0.2 mmol) was dissolved in 15 mL of acetone, 47% HBr methanol solution (0.046 mL, 0.4 mmol) was added, degassed and stirred at room temperature for 30 minutes. After removing the solvent, the residue was used for next reaction without purification.

(3) The synthesis of RuBr$_2$[(S,S)-xylskewphos](3,4-Me$_2$pica)

In a 50 mL Schlenk tube RuBr$_2$[(S,S)-xylskewphos] complex (163 mg. 0.2 mmol) and 2-aminomethyl-3,4-dimethylpyridine (27.3 mg. 0.2 mmol) were placed, and replaced with argon gas. Then dimethylformamide (5 mL) was added, degassed and stirred overnight at room temperature. The reaction solution was filtered through a glass filter filled with silica gel, then the solvent was removed to give 184 mg of RuBr$_2$[(S,S)-xylskewphos] (3,4-Me$_2$pica) (97% yield).

$^{31}$P-NMR spectrum (161.7 MHz, C$_6$D$_6$):δ 63.7 (d, J=44 Hz), 45.7 (d, J=43 Hz)

Synthetic Examples 9 to 14

The Synthesis of Ruthenium XylSKEWPHOS Complexes with Various PICA Ligands

The ruthenium complexes with other amine ligands were synthesized in similar way as Synthetic Example 8 (3) except that amine ligands synthesized in Synthetic Examples 1 to 7 were used instead of 3,4-Me$_2$PICA. The yield was almost quantitative. The results are summarized in the Table below.

TABLE 2

| | Complexes | Amine ligands | $^{31}$P-NMR spectrum (161.83 MHz, C$_6$D$_6$) |
|---|---|---|---|
| Synthetic Example 9 | RuBr$_2$[(S, S)-skewphos] (3,5-Me$_2$pica) | | δ 63.6 ppm (d, J = 39 Hz), 43.3 ppm (d, J = 44 Hz) |
| Synthetic Example 10 | RuBr$_2$[(S, S)-skewphos] (1-amiq) | | δ 62.9 ppm (d, J = 44 Hz), 43.4 ppm (d, J = 44 Hz) |
| Synthetic Example 11 | RuBr$_2$[(S, S)-skewphos] (3-amiq) | | δ 63.4 ppm (d, J = 44 Hz), 43.8 ppm (d, J = 44 Hz) |
| Synthetic Example 12 | RuBr$_2$[(S, S)-skewphos] (2-amq) | | δ 60.2 ppm (d, J = 48 Hz), 45.3 ppm (d, J = 44 Hz) |
| Synthetic Example 13 | RuBr$_2$[(S, S)-skewphos] (2-ampz) | | δ 61.0 ppm (d, J = 44 Hz), 42.5 ppm (d, J = 44 Hz) |
| Synthetic Example 14 | RuBr$_2$[(S, S)-skewphos] (2-ampr) | | δ 62.5 ppm (d, J = 44 Hz), 44.3 ppm (d, J = 44 Hz) |

Working Example 1

The Hydrogenating Reaction of Acetophenone

Acetophenone used was the guaranteed reagent from KANTO CHEMICAL CO., INC., which was used directly.

In an autoclave, 1.32 mg of RuBr$_2$[(S,S)-xylskewphos] (3,5-Me$_2$pica) (1.29×10$^{-3}$ mmol, S/C=10000) and 5.79 mg of potassium tert-butoxide (5.16×10$^{-2}$ mmol) are placed, and replaced with argon gas. Under argon gas flow, 1.5 mL of acetophenone (12.9 mmol) and 2.9 mL of ethanol was added while measuring by a syringe, pressurized with hydrogen to 10 atm, stirred at 40° C. for 19 hours, then the reduction of the hydrogen pressure was confirmed and phenylethanol was obtained at 100% yield. The optical purity was 88.0% ee as measured by GC (CP-Chirasil-DEX CB (0.25 mml. D×25 m, DF=0.25 μm, from VARIAN), constant at 110° C., pressure: 102.0 kPa, column flow: 1.18 mL/min, vaporizing chamber temperature: 250° C., detector temperature: 275° C., the retention time of each enantiomer was: (R): 11.7 min, (S): 12.4 min), and (S) isomer has predominantly been generated.

Comparative Example 1

The reaction was carried out in similar way as Working Example 1 except that the complex was changed to RuBr$_2$[(S,S)-xylskewphos](pica). After the reaction, the reduction in hydrogen pressure was confirmed, and phenylethanol was obtained at 100% yield. The optical purity was 80.3% ee as measured under the analysis condition described in Working Example 1, and (S) isomer has predominantly been generated.

Working Examples 2 to 6

The experiment was carried out in similar way as Working Example 1 except that the reaction solvent and substrate were changed as indicated in the Table below. The results are summarized in the Table below, which also describes the results from Working Example 1.

TABLE 3

| | Ketone substrate | Reaction solvate | Yield (%) | Optical purity (% ee) | Absolute configuration | Analysis condition |
|---|---|---|---|---|---|---|
| Working Example 1 | (phenyl methyl ketone) | ethanol | 100 | 88.0 | S | — |
| Working Example 2 | (2-chlorophenyl methyl ketone) | ethanol | 100 | 96.2 | S | A |
| Working Example 3 | (2-chlorophenyl methyl ketone) | 2-propanol | 100 | 95.8 | S | A |
| Working Example 4 | (4-chlorophenyl methyl ketone) | ethanol | 100 | 82.5 | S | B |
| Working Example 5 | (2-fluorophenyl methyl ketone) | ethanol | 100 | 91.4 | S | C |
| Working Example 6 | (2-methoxyphenyl methyl ketone) | 2-propanol | 93 | 98.9 | S | D |

(Analysis Condition A)
GC (CP-Chirasil-DEX CB (0.25 mml. D×25 m, DF=0.25 μm, from VARIAN)), constant at 140° C., pressure: 102.0 kPa, column flow: 1.04 mL/min, vaporizing chamber temperature: 250° C., detector temperature: 275° C., the retention time of each enantiomer was: (R): 9.1 min, (S): 10.3 min.
(Analysis Condition B)
GC (CP-Chirasil-DEX CB (0.25 mml. D×25 m, DF=0.25 μm, from VARIAN)), constant at 140° C., pressure: 102.0 kPa, column flow: 1.04 mL/min, vaporizing chamber temperature: 250° C., detector temperature: 275° C., the retention time of each enantiomer was: (R): 9.9 min, (S): 10.6 min.
(Analysis Condition C)
GC (CP-Chirasil-DEX CB (0.25 mml. D×25 m, DF=0.25 μm, from VARIAN)), constant at 120° C., pressure: 102.0 kPa, column flow: 1.13 mL/min, vaporizing chamber temperature: 250° C., detector temperature: 275° C., the retention time of each enantiomer was: (R): 8.1 min, (S): 8.5 min.
(Analysis Condition D)
GC(CP-Chirasil-DEX CB (0.25 mml. D×25 m, DF=0.25 μm, from VARIAN)), 110° C. (50 min hold)-(2° C./min)-140° C. (5 min hold), pressure: 102.0 kPa, column flow: 1.18 mL/min, vaporizing chamber temperature: 250° C., detector temperature: 275° C., the retention time of each enantiomer was: (S): 39.5 min, (R): 44.1 min.

Comparative Examples 2 to 7

The reaction was carried out in similar way as Working Example 1 except that the complex was changed to RuBr$_2$[(S,S)-xylskewphos](pica), and the reaction solvent and substrate were changed as indicated in the Table below. The results are summarized in the Table below, which also describes the results from Comparative Example 1. Analysis conditions indicated in the Table is the same as the Table provided from Working Examples 1 to 6. From the results, it is clear that RuBr$_2$[(S,S)-xylskewphos] (3,5-Me$_2$pica) has a better enantioselectivity as compared to RuBr$_2$[(S,S)-xylskewphos](pica) complex.

hydrogen to 10 atm., stirred at 40° C. for 21 hours, and the reduction of hydrogen pressure was confirmed and (S)-1-(2, 6-dichloro-3-fluorophenyl)ethanol was obtained at 100% yield. The optical purity measured by HPLC (DAICEL CHRALPAK AD-RH, acetonitrile/water=25/75, 0.5 mL/min, 25° C., 220 nm, the retention time of each enantiomer: (S): 56.1 min, (R): 64.5 min) was 98.5% ee.

TABLE 4

| | Ketone substrate | Reaction solvate | Yield (%) | Optical purity (% ee) | Absolute configuration | Analysis condition |
|---|---|---|---|---|---|---|
| Comparative Example 2 | acetophenone | ethanol | 100 | 80.3 | S | — |
| Comparative Example 3 | 2'-chloroacetophenone | ethanol | 100 | 92.3 | S | A |
| Comparative Example 4 | 2'-chloroacetophenone | 2-propanol | 100 | 91.2 | S | A |
| Comparative Example 5 | 4'-chloroacetophenone | ethanol | 100 | 70.0 | S | B |
| Comparative Example 6 | 2'-fluoroacetophenone | ethanol | 100 | 83.6 | S | C |
| Comparative Example 7 | 2'-methoxyacetophenone | 2-propanol | 69 | 96.6 | S | D |

Working Example 7

The hydrogenating reaction of 2',6'-dichloro-3'-fluoroacetophenone

In an autoclave, 3.22 mg of RuBr$_2$[(S,S)-xylskewphos](3,5-Me$_2$pica) (3.39×10$^{-3}$ mmol, S/C=1000) and 7.62 mg of potassium tert-butoxide (6.79×10$^{-2}$ mmol) are placed, replaced with argon gas. Under argon gas flow, 0.5 mL of 2',6'-dichloro-3'-fluoroacetophenone (3.39 mmol, from Jiangxi Jixiang Pharmachemical) and 2.9 mL of 2-propanol are added while measuring with syringe, pressurized with Working Examples 8 to 13, Comparative Examples 8, 9

The reaction was carried out under similar condition as Working Example 7 except that the type of the complex was changed. Also, an example in which the complex was changed to RuBr$_2$[(S,S)-xylskewphos](pica) under the same condition is shown in Comparative Example 8, and an example in which the complex was changed to RuBr$_2$[(S,S)-skewphos](pica) is shown in Comparative Example 9. It was elucidated that the use of the ligand described in the general formula (3) improves the enantioselectivity as compared to the ruthenium complex with known PICA-type ligand.

TABLE 5

| | Complex | S/C | Yield (%) | Optical purity (% ee) | Absolute configuration |
|---|---|---|---|---|---|
| Working Example 8 | RuBr$_2$[(S,S)-xylskewphos] (3,4-Me$_2$pica) | 1000 | 100 | 97.2 | S |
| Working Example 9 | RuBr$_2$[(S,S)-xylskewphos] (1-amiq) | 1000 | 100 | 97.6 | S |
| Working Example 10 | RuBr$_2$[(S,S)-xylskewphos] (3-amiq) | 1000 | 100 | 98.2 | S |
| Working Example 11 | RuBr$_2$[(S,S)-xylskewphos] (2-amq) | 1000 | 100 | 96.3 | S |
| Working Example 12 | RuBr$_2$[(S,S)-skewphos] (2-ampz) | 1000 | 100 | 96.2 | S |
| Working Example 13 | RuBr$_2$[(S,S)-skewphos] (2-ampr) | 1000 | 96 | 92.9 | S |
| Comparative Example 8 | RuBr$_2$[(S,S)-xylskewphos] (pica) | 1000 | 100 | 94.0 | S |
| Comparative Example 9 | RuBr$_2$[(S,S)-skewphos] (pica) | 1000 | 100 | 86.0 | S |

Working Examples 14 to 21

For the purpose of improving reaction efficiency, the reaction was carried out under similar condition as Working Example 7 except that two types of complexes: RuBr$_2$[(S,S)-xylskewphos] (3,5-Me$_2$pica) and RuBr$_2$[(S,S)-xylskewphos] (3,5-Me$_2$pica) were used under the conditions of S/C=20000 and the substrate concentration of 2.0 mol/L, and that the concentration of potassium tert-butoxide (KOtBu) was changed. From the results, it was confirmed that the substrate is hydrogenated almost quantitatively under the condition of S/C=20000.

All generated alcohols contain (S) isomers as principal component.

TABLE 6

| | Complex | KOtBu conc. (mmol/L) | Yield (%) | Optical purity (% ee) |
|---|---|---|---|---|
| Working Example 14 | RuBr$_2$[(S,S)-xylskewphos] (3,5-Me$_2$pica) | 20 | 72 | 98.0 |
| Working Example 15 | RuBr$_2$[(S,S)-xylskewphos] (3,5-Me$_2$pica) | 30 | 91 | 98.2 |
| Working Example 16 | RuBr$_2$[(S,S)-xylskewphos] (3,5-Me$_2$pica) | 35 | 85 | 98.1 |
| Working Example 17 | RuBr$_2$[(S,S)-xylskewphos] (3,5-Me$_2$pica) | 40 | 98 | 98.2 |
| Working Example 18 | RuBr$_2$[(S,S)-xylskewphos] (3,5-Me$_2$pica) | 50 | 99 | 98.2 |
| Working Example 19 | RuBr$_2$[(S,S)-xylskewphos] (3-amiq) | 20 | 52 | 97.8 |
| Working Example 20 | RuBr$_2$[(S,S)-xylskewphos] (3-amiq) | 30 | 88 | 98.1 |
| Working Example 21 | RuBr$_2$[(S,S)-xylskewphos] (3-amiq) | 40 | 77 | 98.0 |

The invention claimed is:

1. A method for producing optically active secondary alcohols, the method comprising:

reacting a substrate carbonyl compound selected from the group consisting of aromatic ketones and heteroaromatic ketones, and these ketones in which the aromatic ring or heterocycle has a substituent, with hydrogen and/or a hydrogen donating compound in the presence of one or more ruthenium complexes selected by the compounds expressed by following general formula (1):

where,

X and Y are the same or different from each other and denote a hydrogen atom or an anionic group;

A denotes an optically active diphosphine expressed by following general formula (2)

where,

R$^1$ and R$^2$ are the same or different from each other and denote a C1-20 chained or cyclic hydrocarbon group which may have a substituent;

R$^3$ and R$^4$ are the same or different from each other and denote a hydrogen atom or a C1-3 hydrocarbon group;

R$^5$, R$^6$, R$^7$ and R$^8$ are the same or different from each other and denote a hydrocarbon group which may have a substituent; and,

* expresses an asymmetric carbon atom;

B denotes an amine compound expressed by following general formula (3):

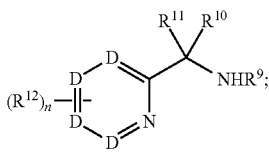

where,
each D is independently selected as a carbon atom or nitrogen atom;
$R^9$, $R^{10}$ and $R^{11}$ are the same or different from each other and denote a hydrogen atom or a C1-20 chained or cyclic hydrocarbon group which may have a substituent, and/or, $R^{10}$ and $R^{11}$ are connected to each other to form a saturated or unsaturated hydrocarbon ring or heterocycle which may have a substituent;
each $R^{12}$ is the same or different from each other and denotes a C1-20 chained or cyclic hydrocarbon group which may have a substituent, and/or, the adjacent $R^{12}$ are connected to each other to form a saturated or unsaturated hydrocarbon ring or heterocycle which may have a substituent;
$R^{12}$ may at least partly be bound to ruthenium as an anionic group X;
n is an integer ranging from 0 to (4−m) and represents the number of $R^{12}$ substituents in formula (3); and,
m is an integer ranging from 0 to 4 and represents the number of Ds that are selected as nitrogen atoms in formula (3),
provided that n is an integer ranging from 2 to 4 when m is 0.

2. The method according to claim 1, further comprising:
preparing a ruthenium complex expressed by the general formula (1) in situ in the presence of:
one or more complexes selected from the compounds expressed by following general formula (4):

RuXYA    (4);

where,
X and Y are the same or different from each other and denote a hydrogen atom or an anionic group;
A denotes an optically active diphosphine expressed by following general formula (2);

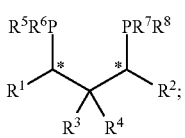

where,
$R^1$ and $R^2$ are the same or different from each other and denote a C1-20 chained or cyclic hydrocarbon group which may have a substituent;
$R^3$ and $R^4$ are the same or different from each other and denote a hydrogen atom or a C1-3 hydrocarbon group;
$R^5$, $R^6$, $R^7$ and $R^8$ are the same or different from each other and denote a hydrocarbon group which may have a substituent; and,

* expresses an asymmetric carbon atom;
and,
one or more amine compound selected from the compounds expressed by the above described general formula (3).

3. The method according to claim 1, wherein n is 2 or more than 2.

4. The method according to claim 3, wherein
the adjacent $R^{12}$ groups are connected to each other to form a saturated or unsaturated hydrocarbon ring or heterocycle which may have a substituent; and,
a quinoline or isoquinoline ring system is formed with the ring formed by the adjacent $R^{12}$ groups and the ring comprising D.

5. The method according to claim 1 wherein, in the general formula (3), one or more of the four D are nitrogen atoms.

6. The method according to claim 1, wherein A is selected from the group consisting of 2,4-bis(diphenylphosphino)pentane, 2,4-bis(di-4-tolylphosphino)pentane, 2,4-bis(di-3,5-xylylphosphino)pentane, 2,4-bis(di-4-tert-butylphenylphosphino)pentane, 2,4-bis(di-4-isopropylphenylphosphino)pentane, 2,4-bis(di-3,5-diethylphenylphosphino)pentane, 2,4-bis(di-3,5-diisopropylphenylphosphino)pentane, 2,4-bis(diphenylphosphino)-3-methylpentane, 2,4-bis(di-4-tolylphosphino)-3-methylpentane, 2,4-bis(di-3,5-xylylphosphino)-3-methylpentane, 2,4-bis(di-4-tert-butylphenylphosphino)-3-methylpentane, 2,4-bis(di-3,5-diethylphenylphosphino)-3-methylpentane, 2,4-bis(di-3,5-diisopropylphenylphosphino)-3-methylpentane, 1,3-bis(diphenylphosphino)-1,3-diphenylpropane, 1,3-bis(di-4-tolylphosphino)-1,3-diphenylpropane, 1,3-bis(di-3,5-xylylphosphino)-1,3-diphenylpropane, 1,3-bis(di-4-tert-butylphenylphosphino)-1,3-diphenylpropane, 1,3-bis(di-3,5-diethylphenylphosphino)-1,3-diphenylpropane, 1,3-bis(di-3,5-diisopropylphenylphosphino)-1,3-diphenylpropane, 1,3-bis(diphenylphosphino)-1,3-diphenyl-2-methylpropane, 1,3-bis(di-4-tolylphosphino)-1,3-diphenyl-2-methylpropane, 1,3-bis(di-3,5-xylylphosphino)-1,3-diphenyl-2-methylpropane, 1,3-bis(di-4-tert-butylphenylphosphino)-1,3-diphenyl-2-methylpropane, 1,3-bis(di-3,5-diethylphenylphosphino)-1,3-diphenyl-2-methylpropane and 1,3-bis(di-3,5-diisopropylphenylphosphino)-1,3-diphenyl-2-methylpropane.

7. The method according to claim 1, wherein A is selected from the group consisting of 2,4-bis(diphenylphosphino)pentane, 2,4-bis(di-4-tolylphosphino)pentane, 2,4-bis(di-3,5-xylylphosphino)pentane, 2,4-bis(di-4-isopropylphenylphosphino)pentane, 2,4-bis(di-4-tert-butylphenylphosphino)pentane, 2,4-bis(di-3,5-diethylphenylphosphino)pentane and 2,4-bis(diphenylphosphino)-3-methylpentane.

8. The method according to claim 1, wherein B is selected from the group consisting of 2-(aminomethyl)-3,4-dimethylpyridine, 2-(aminomethyl)-3,5-dimethylpyridine, 2-(aminomethyl)-3,6-dimethylpyridine, 2-(aminomethyl)-4,5-dimethylpyridine, 2-(aminomethyl)-4,6-dimethylpyridine, 2-(aminomethyl)-5,6-dimethylpyridine, 2-(aminomethyl)-3,4,5-trimethylpyridine, 2-(aminomethyl)-3,5,6-trimethylpyridine, 2-(aminomethyl)-4,5,6-trimethylpyridine, 2-(aminomethyl)-3,4,5,6-tetramethylpyridine, 2-(aminomethyl)-3,4-diethylpyridine, 2-(aminomethyl)-3,5-diethylpyridine, 2-(aminomethyl)-3,6-diethylpyridine, 2-(aminomethyl)-4,5-diethylpyridine, 2-(aminomethyl)-4,6-diethylpyridine, 2-(aminomethyl)-5,6-diethylpyridine, 2-(aminomethyl)-3,4-di n-propylpyridine, 2-(aminomethyl)-3,5-di n-propylpyridine, 2-(aminomethyl)-3,6-di n-propylpyridine, 2-(aminomethyl)-4,5-di n-propylpyridine, 2-(aminomethyl)-4,6-di n-propylpyridine, 2-(aminomethyl)-5,6-di n-propylpyridine, 2-(aminomethyl)-3,4-diisopropylpyridine, 2-(aminomethyl)-3,5-diisopropylpyridine, 2-(aminomethyl)-3,6-diisopropylpyridine, 2-(aminomethyl)-4,5-diisopropylpyridine, 2-(aminomethyl)-4,6-diisopropylpyridine, 2-(aminomethyl)-5,6-diisopropylpyridine, 2-(aminomethyl)-3,4-di n-butylpyridine, 2-(aminomethyl)-3,5-di n-butylpyridine, 2-(aminomethyl)-3,6-di n-butylpyridine, 2-(aminomethyl)-4,5-di n-butylpyridine, 2-(aminomethyl)-4,6-di n-butylpyridine, 2-(aminomethyl)-5,6-di n-butylpyridine, 2-(aminomethyl)-3,4-diisobutylpyridine, 2-(aminomethyl)-3,5-diisobutylpyridine, 2-(aminomethyl)-3,6-diisobutylpyridine, 2-(aminomethyl)-4,5-diisobutylpyridine, 2-(aminomethyl)-4,6-diisobutylpyridine, 2-(aminomethyl)-5,6-diisobutylpyridine, 2-(aminomethyl)-3,4-di tert-butylpyridine, 2-(aminomethyl)-3,5-di tert-butylpyridine, 2-(aminomethyl)-3,6-di tert-butylpyridine, 2-(aminomethyl)-4,5-di tert-butylpyridine, 2-(aminomethyl)-4,6-di tert-butylpyridine, 2-(aminomethyl)-5,6-di tert-butylpyridine, 2-(aminomethyl)-3,4-diphenylpyridine, 2-(aminomethyl)-3,5-diphenylpyridine, 2-(aminomethyl)-3,6-diphenylpyridine, 2-(aminomethyl)-4,5-diphenylpyridine, 2-(aminomethyl)-4,6-diphenylpyridine, 2-(aminomethyl)-5,6-diphenylpyridine, 2-(aminomethyl)quinoline, 1-(aminomethyl)isoquinoline, 3-(aminomethyl)isoquinoline, 2-2-(aminomethyl)pyradine, 2-(aminomethyl)pyrimidine, 6-aminomethylphenanthridine, 2-(1-aminoethyl)-3,4-dimethylpyridine, 2-(1-aminoethyl)-3,5-dimethylpyridine, 2-(1-aminoethyl)-3,6-dimethylpyridine, 2-(1-aminoethyl)-4,5-dimethylpyridine, 2-(1-aminoethyl)-4,6-dimethylpyridine, 2-(1-aminoethyl)-5,6-dimethylpyridine, 2-(1-aminoethyl)-3,4,5-trimethylpyridine, 2-(1-aminoethyl)-3,5,6-trimethylpyridine, 2-(1-aminoethyl)-4,5,6-trimethylpyridine, 2-(1-aminoethyl)-3,4,5,6-tetramethylpyridine, 2-(1-aminoethyl)-3,4-diethylpyridine, 2-(1-aminoethyl)-3,5-diethylpyridine, 2-(1-aminoethyl)-3,6-diethylpyridine, 2-(1-aminoethyl)-4,5-diethylpyridine, 2-(1-aminoethyl)-4,6-diethylpyridine, 2-(1-aminoethyl)-5,6-diethylpyridine, 2-(1-aminoethyl)-3,4-di n-propylpyridine, 2-(1-aminoethyl)-3,5-di n-propylpyridine, 2-(1-aminoethyl)-3,6-di n-propylpyridine, 2-(1-aminoethyl)-4,5-di n-propylpyridine, 2-(1-aminoethyl)-4,6-di n-propylpyridine, 2-(1-aminoethyl)-5,6-di n-propylpyridine, 2-(1-aminoethyl)-3,4-diisopropylpyridine, 2-(1-aminoethyl)-3,5-diisopropylpyridine, 2-(1-aminoethyl)-3,6-diisopropylpyridine, 2-(1-aminoethyl)-4,5-diisopropylpyridine, 2-(1-aminoethyl)-4,6-diisopropylpyridine, 2-(1-aminoethyl)-5,6-diisopropylpyridine, 2-(1-aminoethyl)-3,4-di n-butylpyridine, 2-(1-aminoethyl)-3,5-di n-butylpyridine, 2-(1-aminoethyl)-3,6-di n-butylpyridine, 2-(1-aminoethyl)-4,5-di n-butylpyridine, 2-(1-aminoethyl)-4,6-di n-butylpyridine, 2-(1-aminoethyl)-5,6-di n-butylpyridine, 2-(1-aminoethyl)-3,4-diisobutylpyridine, 2-(1-aminoethyl)-3,5-diisobutylpyridine, 2-(1-aminoethyl)-3,6-diisobutylpyridine, 2-(1-aminoethyl)-4,5-diisobutylpyridine, 2-(1-aminoethyl)-4,6-diisobutylpyridine, 2-(1-aminoethyl)-5,6-diisobutylpyridine, 2-(1-aminoethyl)-3,4-di tert-butylpyridine, 2-(1-aminoethyl)-3,5-di tert-butylpyridine, 2-(1-aminoethyl)-3,6-di tert-butylpyridine, 2-(1-aminoethyl)-4,5-di tert-butylpyridine, 2-(1-aminoethyl)-4,6-di tert-butylpyridine, 2-(1-aminoethyl)-5,6-di tert-butylpyridine, 2-(1-aminoethyl)-3,4-diphenylpyridine, 2-(1-aminoethyl)-3,5-diphenylpyridine, 2-(1-aminoethyl)-3,6-diphenylpyridine, 2-(1-aminoethyl)-4,5-diphenylpyridine, 2-(1-aminoethyl)-4,6-diphenylpyridine, 2-(1-aminoethyl)-5,6-diphenylpyridine, 2-(1-aminoethyl)quinoline, 1-(1-aminoethyl)isoquinoline, 3-(1-aminoethyl)isoquinoline, 2-(1-aminoethyl)pyradine, 2-(1-aminoethyl)pyrimidine and 6-(1-aminoethyl)phenanthridine.

9. A method for producing optically active secondary alcohols, the method comprising:
reacting a substrate carbonyl compound selected from the group consisting of aromatic ketones and heteroaromatic ketones, and these ketones in which the aromatic ring or heterocycle has a substituent, with hydrogen and/or a hydrogen donating compound in the presence of one or more complexes selected from the compounds expressed by following general formula (4):

RuXYA  (4);

where,
X and Y are the same or different from each other and denote a hydrogen or an anionic group,
A denotes an optically active diphosphine expressed by following general formula (2):

(2)

where,
$R^1$ and $R^2$ are the same or different from each other and denotes a C1-20 chained or cyclic hydrocarbon group which may have a substituent;
$R^3$ and $R^4$ are the same or different from each other and denote a hydrogen atom or a C1-3 hydrocarbon group;
$R^5$, $R^6$, $R^7$ and $R^8$ are the same or different from each other and denote a hydrocarbon group which may have a substituent;
* expresses an asymmetric carbon atom; and,
one or more amine compound selected from the compounds expressed by following general formula (3):

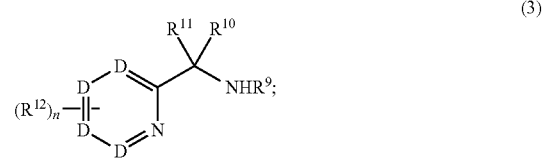

(3)

where,
each D is independently selected as a carbon atom or nitrogen atom;
$R^9$, $R^{10}$ and $R^{11}$ are the same or different from each other, denote a hydrogen atom or a C1-20 chained or cyclic hydrocarbon group which may have a substituent, and/or, $R^{10}$ and $R^{11}$ are connected to each other to form a saturated or unsaturated hydrocarbon ring or heterocycle which may have a substituent;
each $R^{12}$ is the same or different from each other and denotes a C1-20 chained or cyclic hydrocarbon group which may have a substituent, and/or, the adjacent $R^{12}$ are connected to each other to form a saturated or unsaturated hydrocarbon ring or heterocycle which may have a substituent;
$R^{12}$ may at least partly be bound to ruthenium as an anionic group X;
n is an integer ranging from 0 to (4−m) and represents the number of $R^{12}$ substituents in formula (3); and, m is an integer ranging from 0 to 4 and represents the number of Ds that are selected as nitrogen atoms in formula (3), provided that n is an integer ranging from 2 to 4 when m is 0.

10. The method of claim 1, wherein the reacting includes reacting the substrate carbonyl compound with hydrogen.

11. The method of claim 1, wherein the reacting includes reacting the substrate carbonyl compound with hydrogen in the presence of a base.

12. The method according to claim 1, the substrate carbonyl compound is an aromatic ketone having a ring selected from the group consisting of a benzene ring and a naphthalene ring.

13. The method according to claim 1, the substrate carbonyl compound is an heteroaromatic ketone having a ring selected from the group consisting of a pyridine ring, pyradine ring, pyrimidine ring, furan ring and thiophene ring.

14. The method according to claim 1, the substrate carbonyl compound is selected from the group consisting of 2'-fluoroacetophenone, 2'-chloroacetophenone, 2'-bromoacetophenone, 2'-iodoacetophenone, 2'-methylacetophenone, 2'-ethylacetophenone, 2'-isopropylacetophenone, 2'-methoxyacetophenone, 2',6'-difluoroacetophenone, 2',6'-dichloroacetophenone, 2',6'-bromoacetophenone, 2',6'-iodoacetophenone, 2',6'-dimethylacetophenone, 2',6'-diethylacetophenone, 2',6'-diisopropylacetophenone, 2',6'-dimethoxyacetophenone, 2',6'-dichloro-3'-fluoroacetophenone, 2',4',6'-trimethylacetophenone, 2',4',6'-trimethoxyacetophenone, and 2',6'-bis(trifluoromethyl)acetophenone.

15. The method according to claim 9, the substrate carbonyl compound is an aromatic ketone having a ring selected from the group consisting of a benzene ring and a naphthalene ring.

16. The method according to claim 9, the substrate carbonyl compound is an heteroaromatic ketone having a ring selected from the group consisting of a pyridine ring, pyradine ring, pyrimidine ring, furan ring and thiophene ring.

17. The method according to claim 9, the substrate carbonyl compound is selected from the group consisting of 2'-fluoroacetophenone, 2'-chloroacetophenone, 2'-bromoacetophenone, 2'-iodoacetophenone, 2'-methylacetophenone, 2'-ethylacetophenone, 2'-isopropylacetophenone, 2'-methoxyacetophenone, 2',6'-difluoroacetophenone, 2',6'-dichloroacetophenone, 2',6'-bromoacetophenone, 2',6'-iodoacetophenone, 2',6'-dimethylacetophenone, 2',6'-diethylacetophenone, 2',6'-diisopropylacetophenone, 2',6'-dimethoxyacetophenone, 2',6'-dichloro-3'-fluoroacetophenone, 2',4',6'-trimethylacetophenone, 2',4',6'-trimethoxyacetophenone, and 2',6'-bis(trifluoromethyl)acetophenone.

* * * * *